(12) United States Patent  (10) Patent No.: US 11,911,512 B2
Huang  (45) Date of Patent: *Feb. 27, 2024

(54) ENCASED TAMPER RESISTANT CONTROLLED RELEASE DOSAGE FORMS

(71) Applicant: Purdue Pharma L.P., Stamford, CT (US)

(72) Inventor: Haiyong Hugh Huang, Princeton, NJ (US)

(73) Assignee: Purdue Pharma L.P., Stamford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/096,686

(22) Filed: Jan. 13, 2023

(65) Prior Publication Data

US 2023/0301921 A1  Sep. 28, 2023

Related U.S. Application Data

(60) Continuation of application No. 17/185,221, filed on Feb. 25, 2021, now Pat. No. 11,590,082, which is a continuation of application No. 16/662,745, filed on Oct. 24, 2019, now Pat. No. 10,966,932, which is a continuation of application No. 15/681,906, filed on Aug. 21, 2017, now abandoned, which is a continuation of application No. 15/045,975, filed on Feb. 17, 2016, now Pat. No. 9,750,703, which is a continuation of application No. 14/024,360, filed on Sep. 11, 2013, now Pat. No. 9,744,136, which is a division of application No. 13/333,560, filed on Dec. 21, 2011, now Pat. No. 8,808,740.

(60) Provisional application No. 61/426,306, filed on Dec. 22, 2010.

(51) Int. Cl.
| | |
|---|---|
| *A61K 9/20* | (2006.01) |
| *A61K 9/24* | (2006.01) |
| *A61K 31/485* | (2006.01) |
| *A61K 9/00* | (2006.01) |
| *A61K 9/28* | (2006.01) |

(52) U.S. Cl.
CPC .......... *A61K 9/2077* (2013.01); *A61K 9/0053* (2013.01); *A61K 9/209* (2013.01); *A61K 9/2031* (2013.01); *A61K 9/2054* (2013.01); *A61K 9/2086* (2013.01); *A61K 9/28* (2013.01); *A61K 31/485* (2013.01)

(58) Field of Classification Search
None
See application file for complete search history.

(56) References Cited

U.S. PATENT DOCUMENTS

| | | |
|---|---|---|
| 3,065,143 A | 11/1962 | Christenson |
| 3,096,248 A | 7/1963 | Rudzki |
| 3,133,132 A | 5/1964 | Sidney |
| 3,149,038 A | 9/1964 | Jeffries |
| 3,173,876 A | 3/1965 | Zobrist |
| 3,260,646 A | 7/1966 | Frederik |
| 3,276,586 A | 10/1966 | Rosaen |
| 3,400,197 A | 9/1968 | Irwin |
| 3,541,005 A | 11/1970 | Strathmann |
| 3,541,006 A | 11/1970 | Bixler |
| 3,546,876 A | 12/1970 | Fokker |
| 3,845,770 A | 11/1974 | Theeuwes |
| 3,879,555 A | 4/1975 | Pachter |
| 3,916,889 A | 11/1975 | Russell |
| 3,965,256 A | 6/1976 | Leslie |
| 3,980,766 A | 9/1976 | Shaw |
| 4,063,064 A | 12/1977 | Saunders |
| 4,070,494 A | 1/1978 | Hoffmeister |
| 4,088,864 A | 5/1978 | Theeuwes |
| 4,160,020 A | 7/1979 | Ayer |
| 4,175,119 A | 11/1979 | Porter |
| 4,200,098 A | 4/1980 | Ayer |
| 4,235,870 A | 11/1980 | Leslie |
| 4,285,987 A | 8/1981 | Ayer |
| 4,293,539 A | 10/1981 | Ludwig |
| 4,366,310 A | 12/1982 | Leslie |
| 4,385,057 A | 5/1983 | Bjork |
| 4,389,393 A | 6/1983 | Schor et al. |

(Continued)

FOREIGN PATENT DOCUMENTS

| | | |
|---|---|---|
| CA | 2569743 C | 10/2013 |
| EP | 0111144 B1 | 12/1986 |

(Continued)

OTHER PUBLICATIONS

Gemmation et al. (Effectiveness and Safety of New Oxycodone/Acetaminophen Formulations with Reduced Acetaminophen for the treatment of Low Back Pain, Pain Medicine, vol. 4, No. 1, 2003). (Year: 2003).*
"Guidance for Industry, Food-Effect Bioavailability and Fed Bioequivalence Studies," U.S. Department of Health and Human Services, Food and Drug Administration, Dec. 2002, 9 pgs.
A Wade and P. J. Weller, Handbook of Pharmaceutical Excipients, 2nd ed., 1994, at 280-282.
Ansel (1985), Peroral Solids< Capsules, Tablets, and Controlled-Release Dosage Forms, pp. 171-172.

(Continued)

*Primary Examiner* — Melissa S Mercier
(74) *Attorney, Agent, or Firm* — Lowenstein Sandler LLP

(57) ABSTRACT

In certain embodiments, the present invention is directed to a solid controlled release dosage form comprising: a core comprising a first portion of an opioid analgesic dispersed in a first matrix material; and a shell encasing the core and comprising a second portion of the opioid analgesic dispersed in a second matrix material; wherein the amount of opioid analgesic released from the dosage form is proportional within 20% to elapsed time from 8 to 24 hours, as measured by an in-vitro dissolution in a USP Apparatus 1 (basket) at 100 rpm in 900 ml simulated gastric fluid without enzymes (SGF) at 37 C.

20 Claims, 5 Drawing Sheets

(56) References Cited

U.S. PATENT DOCUMENTS

| | | |
|---|---|---|
| 4,424,205 A | 1/1984 | LaHann |
| 4,443,428 A | 4/1984 | Oshlack |
| 4,457,933 A | 7/1984 | Gordon |
| 4,459,278 A | 7/1984 | Porter |
| 4,588,580 A | 5/1986 | Gale et al. |
| 4,599,342 A | 7/1986 | LaHann |
| 4,610,870 A | 9/1986 | Jain |
| 4,612,008 A | 9/1986 | Wong |
| 4,629,623 A | 12/1986 | Balazs |
| 4,666,705 A | 5/1987 | DeCrosta |
| 4,764,378 A | 8/1988 | Keith |
| 4,765,989 A | 8/1988 | Wong |
| 4,769,372 A | 9/1988 | Kreek |
| 4,785,000 A | 11/1988 | Kreek |
| 4,806,341 A | 2/1989 | Chien |
| 4,812,446 A | 3/1989 | Brand |
| 4,834,984 A | 5/1989 | Goldie |
| 4,844,909 A | 7/1989 | Goldie |
| 4,861,598 A | 8/1989 | Oshlack |
| 4,867,985 A | 9/1989 | Heafield |
| 4,957,681 A | 9/1990 | Klimesch |
| 4,970,075 A | 11/1990 | Oshlack |
| 4,990,341 A | 2/1991 | Goldie |
| 4,992,277 A | 2/1991 | Sangekar |
| 5,026,556 A | 6/1991 | Drust |
| 5,059,600 A | 10/1991 | Gawin |
| 5,069,909 A | 12/1991 | Sharma |
| 5,111,942 A | 5/1992 | Bernardin |
| 5,113,585 A | 5/1992 | Rogers |
| 5,114,942 A | 5/1992 | Gawin |
| 5,130,311 A | 7/1992 | Guillaumet |
| 5,149,538 A | 9/1992 | Granger |
| 5,169,645 A | 12/1992 | Shukla |
| 5,202,128 A | 4/1993 | Morella |
| 5,215,758 A | 6/1993 | Krishnamurthy |
| 5,225,199 A | 7/1993 | Hidaka |
| 5,232,685 A | 8/1993 | Speck |
| 5,232,934 A | 8/1993 | Downs |
| 5,240,711 A | 8/1993 | Hille |
| 5,266,331 A | 11/1993 | Oshlack |
| 5,273,758 A | 12/1993 | Royce |
| 5,273,760 A | 12/1993 | Oshlack |
| 5,286,493 A | 2/1994 | Oshlack |
| 5,290,816 A | 3/1994 | Blumberg |
| 5,300,302 A | 4/1994 | Tachon |
| 5,321,012 A | 6/1994 | Mayer |
| 5,324,351 A | 6/1994 | Oshlack |
| 5,330,766 A | 7/1994 | Morella |
| 5,356,467 A | 10/1994 | Oshlack |
| 5,376,705 A | 12/1994 | Leys |
| 5,378,474 A | 1/1995 | Morella |
| 5,399,351 A | 3/1995 | Leshchiner |
| 5,403,868 A | 4/1995 | Reid |
| 5,407,686 A | 4/1995 | Patel |
| 5,409,944 A | 4/1995 | Black |
| 5,411,745 A | 5/1995 | Oshlack |
| 5,422,123 A | 6/1995 | Conte |
| 5,425,950 A | 6/1995 | Dandiker |
| 5,436,265 A | 7/1995 | Black |
| 5,472,712 A | 12/1995 | Oshlack |
| 5,472,943 A | 12/1995 | Crain |
| 5,474,995 A | 12/1995 | Ducharme |
| 5,478,577 A | 12/1995 | Sackler |
| 5,489,439 A | 2/1996 | Bola |
| 5,500,227 A | 3/1996 | Oshlack |
| 5,502,058 A | 3/1996 | Mayer |
| 5,505,959 A | 4/1996 | Tachon |
| 5,508,042 A | 4/1996 | Oshlack |
| 5,508,043 A | 4/1996 | Krishnamurthy |
| 5,510,368 A | 4/1996 | Lau |
| 5,514,680 A | 5/1996 | Weber |
| 5,521,213 A | 5/1996 | Prasit |
| 5,536,752 A | 7/1996 | Ducharme |
| 5,549,912 A | 8/1996 | Oshlack |
| 5,549,913 A | 8/1996 | Colombo |
| 5,550,142 A | 8/1996 | Ducharme |
| 5,552,422 A | 9/1996 | Gauthier |
| 5,556,838 A | 9/1996 | Mayer |
| 5,567,439 A | 10/1996 | Myers |
| 5,580,578 A | 12/1996 | Oshlack |
| 5,593,694 A | 1/1997 | Hayashida |
| 5,593,695 A | 1/1997 | Merrill |
| 5,593,994 A | 1/1997 | Batt |
| 5,604,253 A | 2/1997 | Lau |
| 5,604,260 A | 2/1997 | Guay |
| 5,616,601 A | 4/1997 | Khanna |
| 5,639,476 A | 6/1997 | Oshlack |
| 5,639,789 A | 6/1997 | Iwasaki |
| 5,654,005 A | 8/1997 | Chen |
| 5,656,295 A | 8/1997 | Oshlack |
| 5,667,805 A | 9/1997 | Merrill |
| 5,676,972 A | 10/1997 | Galiatsatos |
| 5,679,650 A | 10/1997 | Fukunaga |
| 5,681,585 A | 10/1997 | Oshlack |
| 5,695,781 A | 12/1997 | Zhang |
| 5,702,725 A | 12/1997 | Merrill |
| 5,730,716 A | 3/1998 | Beck |
| 5,741,524 A | 4/1998 | Staniforth |
| 5,762,963 A | 6/1998 | Byas-Smith |
| 5,766,623 A | 6/1998 | Ayres |
| 5,788,987 A | 8/1998 | Busetti |
| 5,811,126 A | 9/1998 | Krishnamurthy |
| 5,811,388 A | 9/1998 | Friend |
| 5,814,336 A | 9/1998 | Kelm |
| 5,837,379 A | 11/1998 | Chen |
| 5,843,480 A | 12/1998 | Miller |
| 5,849,240 A | 12/1998 | Miller |
| 5,866,161 A | 2/1999 | Childers |
| 5,866,164 A | 2/1999 | Kuczynski |
| 5,879,705 A | 3/1999 | Heafield |
| 5,891,471 A | 4/1999 | Miller |
| 5,891,919 A | 4/1999 | Blum |
| 5,914,131 A | 6/1999 | Merrill |
| 5,945,125 A | 8/1999 | Kim |
| 5,948,787 A | 9/1999 | Merrill |
| 5,958,452 A | 9/1999 | Oshlack |
| 5,958,459 A | 9/1999 | Chasin |
| 5,965,161 A | 10/1999 | Oshlack |
| 5,965,163 A | 10/1999 | Miller |
| 5,968,551 A | 10/1999 | Oshlack |
| 6,024,982 A | 2/2000 | Oshlack |
| 6,103,261 A | 8/2000 | Chasin |
| 6,120,751 A | 9/2000 | Unger |
| 6,120,803 A | 9/2000 | Wong |
| 6,124,282 A | 9/2000 | Sellers |
| 6,126,969 A | 10/2000 | Shah |
| 6,136,864 A | 10/2000 | Nichols |
| 6,143,322 A | 11/2000 | Sackler |
| 6,153,621 A | 11/2000 | Hamann |
| 6,162,467 A | 12/2000 | Miller |
| 6,210,712 B1 | 4/2001 | Edgren |
| 6,210,714 B1 | 4/2001 | Oshlack |
| 6,223,075 B1 | 4/2001 | Beck |
| 6,228,863 B1 | 5/2001 | Palermo |
| 6,245,357 B1 | 6/2001 | Edgren |
| 6,251,430 B1 | 6/2001 | Zhang |
| 6,277,398 B1 | 8/2001 | Caruso |
| 6,294,194 B1 | 9/2001 | Horhota |
| 6,309,668 B1 | 10/2001 | Bastin |
| 6,348,469 B1 | 2/2002 | Seth |
| 6,352,721 B1 | 3/2002 | Faour |
| 6,365,185 B1 | 4/2002 | Ritschel |
| 6,372,254 B1 | 4/2002 | Ting |
| 6,375,957 B1 | 4/2002 | Kaiko |
| 6,403,056 B1 | 6/2002 | Unger |
| 6,419,954 B1 | 7/2002 | Chu |
| 6,436,441 B1 | 8/2002 | Sako |
| 6,440,464 B1 | 8/2002 | Hsia |
| 6,455,537 B1 | 9/2002 | Cooper |
| 6,485,748 B1 | 11/2002 | Chen |
| 6,488,962 B1 | 12/2002 | Berner |
| 6,488,963 B1 | 12/2002 | McGinity |
| 6,491,949 B2 | 12/2002 | Faour |
| 6,559,159 B2 | 5/2003 | Carroll |

(56) References Cited

U.S. PATENT DOCUMENTS

| | | |
|---|---|---|
| 6,562,375 B1 | 5/2003 | Sako |
| 6,572,885 B2 | 6/2003 | Oshlack |
| 6,593,367 B1 | 7/2003 | Dewey |
| 6,627,635 B2 | 9/2003 | Palermo |
| 6,696,088 B2 | 2/2004 | Oshlack |
| 6,723,340 B2 | 4/2004 | Gusler |
| 6,730,321 B2 | 5/2004 | Ting |
| 6,733,783 B2 | 5/2004 | Oshlack |
| 6,761,895 B2 | 7/2004 | Sawada |
| 6,808,720 B2 | 10/2004 | Unger |
| 6,919,373 B1 | 7/2005 | Lam |
| 6,955,821 B2 | 10/2005 | Davis |
| 6,987,082 B2 | 1/2006 | Tijsma |
| 6,995,169 B2 | 2/2006 | Chapleo |
| 7,056,890 B2 | 6/2006 | Najarian |
| RE39,239 E | 8/2006 | Busetti |
| 7,141,250 B2 | 11/2006 | Oshlack |
| 7,144,587 B2 | 12/2006 | Oshlack |
| 7,157,103 B2 | 1/2007 | Sackler |
| 7,201,920 B2 | 4/2007 | Kumar |
| 7,276,250 B2 | 10/2007 | Baichwal |
| 7,332,182 B2 | 2/2008 | Sackler |
| 7,399,488 B2 | 7/2008 | Hirsh |
| 7,442,387 B2 | 10/2008 | Sugihara |
| 7,510,726 B2 | 3/2009 | Kumar |
| 7,718,194 B2 | 5/2010 | Chenevier |
| 7,727,557 B2 | 6/2010 | Sackler |
| 7,776,314 B2 | 8/2010 | Bartholomaus |
| 7,842,307 B2 | 11/2010 | Oshlack |
| 7,943,174 B2 | 5/2011 | Oshlack |
| 7,981,439 B2 | 7/2011 | Kumar |
| 8,017,148 B2 | 9/2011 | Sackler |
| 8,075,872 B2 | 12/2011 | Arkenau-Maric |
| 8,101,630 B2 | 1/2012 | Kumar |
| 8,114,383 B2 | 2/2012 | Bartholomaus |
| 8,114,384 B2 | 2/2012 | Arkenau |
| 8,143,267 B2 | 3/2012 | Burch |
| 8,192,722 B2 | 6/2012 | Arkenau-Maric |
| 8,193,209 B2 | 6/2012 | Burch |
| 8,293,277 B2 | 10/2012 | Swanson |
| 8,309,060 B2 | 11/2012 | Bartholomaus |
| 8,323,692 B2 | 12/2012 | Frisbee |
| 8,337,888 B2 | 12/2012 | Wright |
| 8,389,007 B2 | 3/2013 | Wright |
| 8,394,408 B2 | 3/2013 | Han |
| 8,409,616 B2 | 4/2013 | Kumar |
| 8,524,275 B2 | 9/2013 | Oshlack |
| 8,529,948 B1 | 9/2013 | Wright |
| 8,551,520 B2 | 10/2013 | Oshlack |
| 8,609,143 B2 | 12/2013 | Fischer |
| 8,609,683 B2 | 12/2013 | Wright |
| 8,617,600 B2 | 12/2013 | Bhatt |
| 8,637,540 B2 | 1/2014 | Kumar |
| 8,647,667 B2 | 2/2014 | Oshlack |
| 8,652,497 B2 | 2/2014 | Sackler |
| 8,652,515 B2 | 2/2014 | Sackler |
| 8,652,529 B2 | 2/2014 | Guimberteau |
| 8,808,740 B2 * | 8/2014 | Huang ............... A61K 9/2031 424/474 |
| 8,871,265 B2 | 10/2014 | Wright |
| 8,999,961 B2 | 4/2015 | Wright |
| 9,034,376 B2 | 5/2015 | Wright |
| 9,040,084 B2 | 5/2015 | Wright |
| 9,044,435 B2 | 6/2015 | Wright |
| 9,060,976 B2 | 6/2015 | Wright |
| 9,393,206 B2 | 7/2016 | Huang |
| 9,492,389 B2 | 11/2016 | McKenna |
| 9,492,391 B2 | 11/2016 | McKenna |
| 9,572,779 B2 | 2/2017 | Huang |
| 9,744,136 B2 * | 8/2017 | Huang ............... A61K 9/2054 |
| 9,750,703 B2 * | 9/2017 | Huang ............... A61K 9/2077 |
| 9,861,584 B2 * | 1/2018 | Huang ............... A61K 9/2086 |
| 9,872,837 B2 | 1/2018 | Huang |
| 10,966,932 B2 * | 4/2021 | Huang ............... A61K 9/28 |
| 11,590,082 B2 * | 2/2023 | Huang ............... A61K 9/209 |
| 2001/0031278 A1 | 10/2001 | Oshlack |
| 2002/0028240 A1 | 3/2002 | Sawada |
| 2002/0044966 A1 | 4/2002 | Bartholomaeus |
| 2002/0187192 A1 | 12/2002 | Joshi |
| 2003/0004177 A1 | 1/2003 | Kao |
| 2003/0021841 A1 | 1/2003 | Matharu |
| 2003/0026838 A1 | 2/2003 | Farrell |
| 2003/0035839 A1 | 2/2003 | Hirsh |
| 2003/0059471 A1 | 3/2003 | Compton |
| 2003/0064099 A1 | 4/2003 | Oshlack |
| 2003/0064122 A1 | 4/2003 | Goldberg |
| 2003/0068276 A1 | 4/2003 | Hughes |
| 2003/0068370 A1 | 4/2003 | Sackler |
| 2003/0068371 A1 | 4/2003 | Oshlack |
| 2003/0068375 A1 | 4/2003 | Wright |
| 2003/0068392 A1 | 4/2003 | Sackler |
| 2003/0082230 A1 | 5/2003 | Baichwal |
| 2003/0091625 A1 | 5/2003 | Hariharan |
| 2003/0092724 A1 | 5/2003 | Kao |
| 2003/0124061 A1 | 7/2003 | Roberts |
| 2003/0124185 A1 | 7/2003 | Oshlack |
| 2003/0125347 A1 | 7/2003 | Anderson |
| 2003/0126428 A1 | 7/2003 | Liu |
| 2003/0170181 A1 | 9/2003 | Midha |
| 2003/0206954 A1 | 11/2003 | Lemer |
| 2003/0232081 A1 | 12/2003 | Doshi |
| 2004/0010000 A1 | 1/2004 | Ayer |
| 2004/0047907 A1 | 3/2004 | Oshlack |
| 2004/0110781 A1 | 6/2004 | Harmon |
| 2004/0126428 A1 | 7/2004 | Hughes |
| 2004/0131552 A1 | 7/2004 | Boehm |
| 2004/0151791 A1 | 8/2004 | Mayo-Alvarez |
| 2004/0224020 A1 | 11/2004 | Schoenhard |
| 2004/0228802 A1 | 11/2004 | Chang |
| 2004/0241234 A1 | 12/2004 | Vilkov |
| 2004/0253310 A1 | 12/2004 | Fischer |
| 2004/0266807 A1 | 12/2004 | Oshlack |
| 2005/0020613 A1 | 1/2005 | Boehm |
| 2005/0031546 A1 | 2/2005 | Bartholomaus |
| 2005/0063909 A1 | 3/2005 | Wright |
| 2005/0106249 A1 | 5/2005 | Hwang |
| 2005/0112067 A1 | 5/2005 | Kumar |
| 2005/0112201 A1 | 5/2005 | Baichwal |
| 2005/0118267 A1 | 6/2005 | Baichwal |
| 2005/0158382 A1 | 7/2005 | Cruz |
| 2005/0163717 A1 | 7/2005 | Anderson |
| 2005/0186139 A1 | 8/2005 | Bartholomaus |
| 2005/0214223 A1 | 9/2005 | Bartholomaeus |
| 2005/0236741 A1 | 10/2005 | Arkenau |
| 2005/0276853 A1 | 12/2005 | Baichwal |
| 2006/0002860 A1 | 1/2006 | Bartholomaus |
| 2006/0018837 A1 | 1/2006 | Preston |
| 2006/0039864 A1 | 2/2006 | Bartholomaus |
| 2006/0165790 A1 | 7/2006 | Walden |
| 2006/0188447 A1 | 8/2006 | Arkenau-Maric |
| 2006/0193782 A1 | 8/2006 | Bartholomaus |
| 2006/0193914 A1 | 8/2006 | Ashworth |
| 2006/0210631 A1 | 9/2006 | Patel |
| 2006/0240107 A1 | 10/2006 | Lenaerts |
| 2006/0251721 A1 | 11/2006 | Cruz |
| 2007/0003616 A1 | 1/2007 | Arkenau-Maric |
| 2007/0003617 A1 | 1/2007 | Fischer |
| 2007/0020335 A1 | 1/2007 | Chen |
| 2007/0110807 A1 | 5/2007 | Vergnault |
| 2007/0166234 A1 | 7/2007 | Kumar |
| 2007/0183980 A1 | 8/2007 | Arkenau-Maric |
| 2007/0264327 A1 | 11/2007 | Kumar |
| 2008/0026060 A1 | 1/2008 | Zerbe |
| 2008/0031901 A1 | 2/2008 | Qiu |
| 2008/0057123 A1 | 3/2008 | Grenier |
| 2008/0063725 A1 | 3/2008 | Guimberteau |
| 2008/0075771 A1 | 3/2008 | Vaughn |
| 2008/0095843 A1 | 4/2008 | Nutalapati |
| 2008/0107732 A1 | 5/2008 | Dharmadhikari |
| 2008/0113025 A1 | 5/2008 | Devane |
| 2008/0175908 A1 | 7/2008 | Liu |
| 2008/0176955 A1 | 7/2008 | Heck |
| 2008/0187581 A1 | 8/2008 | Gore |
| 2008/0254123 A1 | 10/2008 | Fischer |

(56) References Cited

U.S. PATENT DOCUMENTS

| | | |
|---|---|---|
| 2008/0260815 A1 | 10/2008 | Hayes |
| 2008/0260824 A1 | 10/2008 | Nangia |
| 2008/0311191 A1 | 12/2008 | Nangia |
| 2009/0011019 A1 | 1/2009 | Jahagirdar |
| 2009/0022798 A1 | 1/2009 | Rosenberg |
| 2009/0081290 A1 | 3/2009 | McKenna |
| 2009/0169587 A1 | 7/2009 | Baichwal |
| 2009/0215808 A1 | 8/2009 | Yum |
| 2010/0015222 A1 | 1/2010 | Han |
| 2010/0172989 A1 | 7/2010 | Roth |
| 2010/0221293 A1 | 9/2010 | Cruz |
| 2011/0020451 A1 | 1/2011 | Bartholomaus |
| 2011/0262532 A1 | 10/2011 | Oshlack |
| 2012/0164220 A1 | 6/2012 | Huang |
| 2013/0209525 A1 | 8/2013 | Cruz |
| 2013/0217716 A1 | 8/2013 | Wright |
| 2013/0245055 A1 | 9/2013 | Wright |
| 2014/0056979 A1 | 2/2014 | Huang |
| 2014/0213606 A1 | 7/2014 | Wright |
| 2014/0371257 A1 | 12/2014 | Wright |
| 2015/0005331 A1 | 1/2015 | Wright |
| 2015/0031718 A1 | 1/2015 | Wright |
| 2015/0140083 A1 | 5/2015 | Wright |
| 2015/0147391 A1 | 5/2015 | Wright |
| 2015/0148319 A1 | 5/2015 | Wright |
| 2015/0182628 A1 | 7/2015 | Wright |

FOREIGN PATENT DOCUMENTS

| | | |
|---|---|---|
| EP | 0318262 A1 | 5/1989 |
| EP | 0647448 A1 | 4/1995 |
| EP | 0661045 A1 | 5/1995 |
| EP | 1293195 A1 | 3/2003 |
| EP | 1897545 B1 | 9/2009 |
| EP | 2457563 B1 | 3/2017 |
| IN | 200601004 P2 | 4/2006 |
| NZ | 602075 A | 1/2014 |
| WO | 9310765 A1 | 6/1993 |
| WO | 9520947 A1 | 8/1995 |
| WO | 9712605 A1 | 4/1997 |
| WO | 9737689 A2 | 10/1997 |
| WO | 9749384 A1 | 12/1997 |
| WO | 9749385 A1 | 12/1997 |
| WO | 9920255 A1 | 4/1999 |
| WO | 9932119 A1 | 7/1999 |
| WO | 9932120 A1 | 7/1999 |
| WO | 9944591 A1 | 9/1999 |
| WO | 2000033835 A1 | 6/2000 |
| WO | 0107950 A1 | 2/2001 |
| WO | 2001008661 A3 | 3/2001 |
| WO | 2001056544 A2 | 8/2001 |
| WO | 2001058447 A1 | 8/2001 |
| WO | 2002036099 A1 | 5/2002 |
| WO | 2001076576 A3 | 6/2002 |
| WO | 2002087558 A1 | 11/2002 |
| WO | 2002094254 A2 | 11/2002 |
| WO | 2003024430 A1 | 3/2003 |
| WO | 2003035029 A1 | 5/2003 |
| WO | 2003035090 A1 | 5/2003 |
| WO | 2003026743 A3 | 10/2003 |
| WO | 2003015531 A3 | 11/2003 |
| WO | 2003092676 A1 | 11/2003 |
| WO | 2004026283 A1 | 4/2004 |
| WO | 2004037259 A1 | 5/2004 |
| WO | 2004026256 A3 | 7/2004 |
| WO | 2005046727 A2 | 5/2005 |
| WO | 2005053587 A1 | 6/2005 |
| WO | 2005102286 A1 | 11/2005 |
| WO | 2006002884 B1 | 3/2006 |
| WO | 2008011169 A2 | 1/2008 |
| WO | 2008023261 A1 | 2/2008 |
| WO | 2007150074 A3 | 4/2008 |
| WO | 2007150075 A3 | 4/2008 |
| WO | 2009114648 A1 | 9/2009 |
| WO | 20100078486 | 7/2010 |
| WO | 2010141505 A1 | 12/2010 |
| WO | 2012131463 A2 | 10/2012 |
| WO | 2013171146 A1 | 11/2013 |

OTHER PUBLICATIONS

Ansel, Howard C., et al., Pharmaceutical Dosage Forms and Drug Delivery Systems, 7th Edition, 1999, pp. 1-2, 23-163, 179-243, 397-449, 552-562, Lippincott Williams & Wilkins, United States.

Apicella, A., "Poly(ethylene oxide)(PEO) and Different Molecular Weight PEO Blends Monolithic Devices for Drug Release," Biomaterials, vol. 14, No. 2, 1993, pp. 83-90.

Apicella, et al. "Poly(ethylene oxide)(PEO) Constant Release Monolithic Devices," Polymers in Medicine: Biomedical and Pharmaceutical Applications, Chapter 3 (1992), pp. 23-37.

Apicella, et al., "Poly(ethylene oxide)-Based Delivery Systems," Polymeric Drugs and Drug Administration, ACS Symposium Series 545, Chapter 9 (1994), oas. 111-125.

Aulton Michaele., et al., Pharmaceutics, The Science of Dosage Form Design, Reprinted 2000, pp. 1-2, 17-37, 62-80, 131-211, 304-321, 359-380, 550-677, Churchill Livingston, China.

Bailey, Poly(Ethylene Oxide) (1976) ("Bailey 1976") at 37, Tables 4.2 and 4.3.

Bettini, et al., "Translocation of drug particles in HPMC matrix gel layer: effect of drug solubility and influence on release rate," Journal of Controlled Release, vol. 70, No. 3, Feb. 2001, pp. 383-391.

Bhatia, R., "Effect of Molecular Mass, Concentration and Temperature on the Rheological Properties of Non-Newtonian Aqueous Polymeric Solutions," 114, 2011, 202 pgs.

Carraher, Polymer Chemistry (6th ed. 2003) at 73.

Chien, Yie W., et al., "Syringeability of Nonaqueous Parenteral Formulations—Development and Evaluation of Testing Apparatus," Journal of Parenteral Science and Technology, vol. 35, No. 6, Nov. 1981, pp. 281-284.

Coppens et al. Hot Melt Extrusion: Effect of Polymer Selection and Processing on Drug Dissolution (2005) (presented at 32nd Annual Meeting of the Controlled Release Society) at 2.

Coppens et al. Thermal and Rheological Evaluation of Pharmaceutical Excipients for Hot Melt Extrusion (2004) (presented to AAPS) at 2.

Deighan, C.J., et al., "Ehabdomyolysis and Acute Renal Failure Resulting From Alcohol and Drug Abuse," QJ Med., vol. 93, 2000, pp. 29-33.

Dexter, M.B., et al., "The Evaluation of the Force to Expel Oily Injection Vehicles from Syringes," J. Pharm. Pharmacol., vol. 31, Aug. 1979, The Pharmaceutical Society of Great Britain, pp. 497-500.

Dow Polyox brochure—Polyox® Water Soluble Resins NF in Pharmaceutical Applications, Dow Chemical Company, Aug. 2002.

Dow Polyox brochure—Polyox® Water Soluble Resins, Dow Chemical Company, Mar. 2002.

Dow, Degradation of Water-Soluble Resins (2002) at 3.

Expert Report of Chang Ryu, Ph.D., dated Apr. 14, 2017, 22 pgs.

Expert Report of Fernando J. Muzzio, Ph.D., dated Apr. 18, 2017, 226 pgs.

Expert Report of Michael Mayersohn, Ph.D., dated Apr. 17, 2017, 93 pgs.

Poynton, Charles, Digital Video and HDTV Algorithms and Interfaces, The CIE System of Colorimetry, 2003, pp. 228-229, Morgan Kaufmann Publishers, San Francisco, United States.

Prescribing Information for Concerta Extended-Release Tablets, Nov. 2010, pp. 1-9, Ortho-McNeil-Janssen Pharmaceuticals, Inc., Titusville, United States.

Sarkar, N., "Kinetics of thermal gelation of methylcellulose and hydroxypropylmethylcellulose in aqueous solutions," Carbohydrate Polymers, vol. 26, No. 3, Jan. 1995, pp. 195-203.

Sarkar, N., "Thermal Gelation Properties of Methyl and Hydroxypropyl Methylcellulose," Journal of Polymer Science, vol. 24, No. 4, Aug. 1979, pp. 1073-1087.

See http://www.simulations-plus.com/about/ (last visited Apr. 6, 2017).

Stafford, J.W., et al., "Temperature dependence of the disintegration times of compressed tablets containing hydroxypropylcellulose as

(56) References Cited

OTHER PUBLICATIONS binder," Journal of Pharmacy and Pharmacology, vol. 30, No. 1, Sep. 1978, pp. 1-5, John Wiley & Sons, New York, United States.
Syed A Altaf, et al., Bead Compacts. I. Effect of Compression on Maintenance of Polymer Coat Integrity in Multilayered Bead Formulations, 24 Drug Development and Industrial Pharmacy 737, 745-746 (1998).
T.Sawada, et al., A new index, the core erosion ratio, of compression-coated times-release tablets predicts the bioavailability of acetaminophen, 265 Int. J. Pharmaceutics 55 (2003).
The 1997 Physician's Desk Reference ("PDR"), 51 st edition, Nov. 1996, pp. 955-957, 988-989, 2163-2167, 2366-2367, Medical Economics Company, Inc., Montvale, NJ, United States.
The Merck Index, 14th Edition, Entry Nos. 4785, 4803, 6276 and 9566, Whitehouse Station, New Jersey, USA, 2006.
Tough, Paul, "The Alchemy of Oxycontin: From Pain Relief to Drug Addiction," The New York Times, Jul. 29, 2001, 14 pgs.
Toyohiro Sawada, et al., Time release compression-coated core tablet containing nifedipine or chronopharmacotherapy, 280 Int. J. Pharmaceutics 103 (2004).
U.S. Pharmacopeia & National Formulary 24/19, The Standard of Quality, United States Pharmacopeial Convention, Inc., 1999, pp. 1233-1238, 1372-1375, 1941-1951, 2002-2003, 2442-2443, 2493-2498, National Publishing, Philadelphia, PA, United States.
U.S. Pharmacopeia, p. 2206, 1995.
Vicodin®, Physcan Desk Reference, 1997, pp. 1404-1405, 51 st Edition, Medical Economics Company, Inc., Montvale, United States.
Wilkins, Jeffrey, N., "Pharmacotherapy of Schizophrenia Patients with Comorbid Substance Abuse," Schizophrenia Bulletin, vol. 23, No. 2, 1997, pqs. 215-228.
Woodburn, K.R., et al., "Vascular Complications of Injecting Drug Misuse," British Journal of Surgery, 1996, Vo. 83, p. 1329-1334.
Yang, et al., "Characterization of Compressibility and Compactibility of Poly(ethylene oxide) Polymers for Modified Release Application by Compaction Simulator," Journal of Pharmaceutical Sciences, vol. 85, No. 10, Oct. 1996, pp. 1085-1090.
Zhang, F., et al., "Properties of Sustained-Release Tablets Prepared by Hot-Melt Extrusion, " Pharmaceutical Development and Technology, vol. 4, No. 2, pp. 241-250 (1999).
Zhang, Feng, Dissertation: "Hot-Melt Extrusion as a Novel Technology to Prepare Sustained-Release Dosage Forms," The University of Texas at Austin, pp. v-xxv, 1-260, Dec. 1999, UMI Microform 9959618, Bell & Howell Information and Learning Company, Ann Arbor, MI, United States.
M. Mayerson and S. Tannenbaum, "On Reclaiming Data from the Literature: Literature Data "R and R" (Recovery and Reanalysis)" with a commentary by Dr. Gerhard Levy, "Using Other People's Data in Publications", Amer. J. Pharm. Ed., 62, 363-37053 (1998). Macheras (1995) at Ch. 3 at 30.
Maggi, L., et al., "Dissolution Behaviour of Hydrophilic Matrix Tablets Containing Two Different Polyethylene Oxides (PEOs) for the Controlled Release of a Water-Soluble Drug," Biomaterials, vol. 23, DOS. 1113-1119 (2002).
Manas Chanda and Salil Roy, Plastics Technology Handbook 6 (3d ed. 1998) at 6.
Markman Order, Case 1 : 15-cv-00687-GMS, Jul. 17, 2017, 3 pgs.
Markman Order, Case 1:15-cv-00687-GMS, May 10, 2017, 14 pgs.
McConnell (2013) at Ch. 31 at 557.
Medical Economics Company, Inc., The 1997 Physician's Desk Reference ("PDR") entry for OXYCONTIN®, 51 st edition, Nov. 1996, Montvale, NJ pp. 2163-2164.
Meier, Barry, "U.S. Asks Painkiller Maker To Help Curb Wide Abuse," The New York Times, May 1, 2001, 3 pgs.
Modern Pharmaceutics, 3rd Edition, Drugs and The Pharmaceutical Sciences, vol. 72, 1996, pp. 21-73, 75-119, 121-153, 155-178, 333-394, 441-487, 575-609, 727-772, Marcel Dekker, Inc., United States.

Moroni, et al., "Application of Poly(oxyethylene) Homopolymers in Sustained Release Solid Formulation," Drug Dev. And Indus. Pharmacy, 21 (12), pp. 1411-1428 (1995).
Muzzio, Ex. 28, U.S. Pat. No. 8,808,740 Claim Chart, 17 pgs, referenced in the Expert Report of Fernando J Muzzio, P.h.D., dated Apr. 18, 2017, 226 pgs, at p. 213, clause 485.
Muzzio, Ex. 32, "Summary of Disputed and Agreed Upon Constructions of Claim Terms," 5 pgs, referenced in the Expert Report of Fernando J. Muzzio, P_h.D., dated Apr. 18, 2017, 226 pages, at p. 36, footnote 4.
Nishit B. Modi, et al., Single and Multiple-Dose Pharmacokinetics of an Oral Once-a-Day Osmotic Controlled-Release OROS (Methylphenidate HCI) Formulation, 40 J. Clin. Pharmacol. 379 (2000).
Oberlerchner J.T. et al., Overview of Methods for Direct Molar Mass Determination of Cellulose, 20 Molecules 10313-41 (2015).
Opinion & Order filed May 27, 2014, Case 1:04-md-01603-SHS, 24 pgs.
Opposition by ALAFAR against Ecuadorian Patent Application No. SP-2013-12760-PCT, Jul. 10, 2014, 8 pgs.
Opposition by PROCAPS S.A. against Ecuadorian Patent Application No. SP-2013-12760-PCT, Jul. 10, 2014, 10 pgs.
Ortho-McNeil-Janssen Pharmaceuticals, Inc. (2010). Prescribing Information for Concerta Extended-Release Tablets, 9 pgs.
Ozeki et al., Mechanism of medicine release from solid dispersion composed of poly(ethylene oxide)-carboxyvinylpolymer interpolymer complex and pH effect on medicine release, International Journal of Pharmaceutics, 1998, vol. 171, pp. 123-132.
Philip, George, et al., "The Human Nasal Response to Capsaicin," J. Allergy Clin. Immonul., vol. 94, No. 6, Part 1, Dec. 1994, pp. 1035-1045, Mosy-Year Book, Inc., Baltimore, MD, United States.
Physician's Desk Reference 2498 (Medical Economics Data Production Co. 1994).
Physician's Desk Reference 272 (Medical Economics 1946) at 32.
Findings of Fact and Conclusions of Law, In re: Oxycontin Antitrust Litigation, Case 1 :04-md-01603-SHS, Apr. 8, 2015, pp. 1-69.
Gennaro, Alfonso, Remington: The Science and Practice of Pharmacy, 20th Edition, 2000, pp. 1-3, 335-355, 654-666, 669-752, 780-820, 858-929, 995-10004, 1098-1155, 1175-1182, 1395- 1399, 2037-2038, Lippincott Williams & Wilkins, Baltimore, MD, United States.
Hardman, Joel G., et al., Goodman & Gilman's The Pharmacological Basis of Therapeutics, 9th Edition, 1996, pp. 3-27, 521-555, 557-577, McGraw-Hill, United States.
Hariharan, M., and Gupta, V.K., "A Novel Compression-Coated Tablet Dosage Form," Pharmaceutical Technology Yearbook, 2001, Jan. 1, 2001, pp. 14-19.
Hem, Stanley, et al., "Tissue Irritation Evaluation of Potential Parenteral Vehicles," Drug Development Communications, 1 :5, 1974, pp. 471-477, Marcel Dekker, Inc.
Heng, Paul, et al., "Role of Surfactant on Drug Release from Tablets", Drug Development and Industrial Pharmacy, Oct. 20, 2008, pp. 951-962, Taylor & Francis, London, United Kingdom.
Howard S. Smith, Opioid Metabolism, 84 Mayo Clin. Proc. 613 (2009).
Huang, H., et al., "Preparation of Controlled Release Oral Dosage Forms by Low Temperature Melt Extrusion," The AAPS Journal, AAPS PharmaSci, 2000, 2(S1), 3 pgs.
Industrial and Engineering Chemistry I/EC, Golden Anniversary Year 50, Pattern for Progress, vol. 50, No. 1, Jan. 10, 1958, pp. 8-11, American Chemical Society, Easton, PA, United States.
International Preliminary Report on Patentability for International Patent Application No. PCT/IB2011/003152 dated Jul. 4, 2013.
International Search Report and Written Opinion for International Patent Application No. PCT/IB2012/000595 dated Oct. 10, 2012, 12 pgs.
J. W. Barnhart and W. J. Caldwell, Gas Chromatographic Determination of Hydrocodone in Serum, J. Chromatography 130:243 (1977).
Kalant, H., et al., "Death in Amphetamine Users: Causes and Rates," CMA Journal, vol. 112, Feb. 8, 1975, pp. 299-304.
Kibbe, Arthur, H., Ph.D., "Polyethylene Oxide," "Handbook of Pharmaceutical Excipients," 3rd Ed., 2000, at p. 399, Tables I and

(56) References Cited

OTHER PUBLICATIONS

II, The American Pharmaceutical Association, Washington, D.C. and the Pharmaceutical Press, London, UK.

Kim, C., "Drug Release from Compressed Hydrophilic POLYOX-WSR Tablets," Journal of Pharmaceutical Sciences, vol. 84, No. 3, Mar. 1995, pp. 303-306.

Korner et al., "Molecular Information on the Dissolution of Polydisperse Polymers: Mixtures of Long and Short Poly (ethylene oxide)," J. Phys. Chem. B., 109 (23), 11530-11537 (2005).

Lee (1992)—Ping I. Lee, Diffusion Controlled Matrix Systems in Treatise on Controlled Drug Delivery (Agis Kydonieus ed. 1992).

L'Hote-Gaston et al. The Use of Polyethylene Oxide Mixtures to Study Formulation Robustness in Hydrophilic Extended Release Matrix Tablets (2009) at 3.

Lieberman (1982), Pharmaceutical Dosage Forms: Tablets, 3rd ed. Herbert A Lieberman & Leon Lachman, 1982, at 156-162.

Lieberman (1989), Pharmaceutical Dosage Forms (2d ed. 1989) at 131-132, 182-185 and example 4, 247-248, 267.

M. Gibaldi and D. Perrier, Pharmacokinetics, Appendix E, 451-457 (2nd ed.1982).

Handbook of Pharmaceutical Excipients, 1986, pp. 234-239, American Pharmaceutical Association, Washington D.C., United States.

\* cited by examiner

ENCASED TAMPER RESISTANT CONTROLLED RELEASE DOSAGE FORMS

CROSS-REFERENCE TO RELATED APPLICATIONS

This application claims priority to U.S. Provisional Application No. 61/426,306 filed Dec. 22, 2010, the disclosure of which is incorporated by reference in its entirety.

FIELD OF THE INVENTION

The present invention relates to multi-layered pharmaceutical dosage forms that are tamper-resistant and preferably provide substantially zero-order release of the active agent contained therein.

BACKGROUND OF THE INVENTION

Pharmaceutical products are sometimes the subject of abuse. For example, a particular dose of opioid agonist may be more potent when administered parenterally as compared to the same dose administered orally. Some formulations can be tampered with to provide the opioid agonist contained therein for illicit use. Controlled release opioid agonist formulations are sometimes crushed or subject to extraction with solvents (e.g., ethanol) by drug abusers to provide the opioid contained therein for immediate release upon oral or parenteral administration.

Controlled release opioid agonist dosage forms that can liberate a portion of the opioid upon exposure to ethanol can also result in a patient receiving the dose more rapidly than intended if a patient disregards instructions for use and concomitantly uses alcohol with the dosage form.

U.S. Patent Application Publication No. 2009/0081290 discloses tamper-resistant dosage forms that, in certain embodiments, are directed to a solid, oral, extended-release pharmaceutical dosage form comprising an extended-release matrix formulation in the form of a 21076/130 tablet or multi-particulates. The tablet or the individual multi-particulates can be at least flattened without breaking, characterized by a thickness of the tablet or of the individual multi-particulates after flattening which corresponds to no more than about 60% of the thickness of the tablet or the individual multi-particulates before flattening, and wherein the flattened tablet or the flattened multi-particulates provide an in-vitro dissolution rate, when measured in a USP Apparatus 1 (basket) at 100 rpm in 900 ml simulated gastric fluid without enzymes (SGF) at 37° C., having a percent amount of active released at 0.5 hours of dissolution that deviates no more than about 20% points from the corresponding in-vitro dissolution rate of a non-flattened reference tablet or reference multi-particulates.

There continues to exist a need in the art for tamper-resistant pharmaceutical oral dosage forms, wherein said dosage forms preferably provide a release profile of the active agent that is substantially zero order.

All references and publications cited herein are hereby incorporated by reference in their entireties for all purposes.

OBJECTS AND SUMMARY OF THE INVENTION

It is an object of certain embodiments of the present invention to provide a solid controlled release dosage form comprising an active agent (e.g., an opioid analgesic), which is tamper resistant.

It is an object of certain embodiments of the present invention to provide a solid controlled release dosage form comprising an active agent (e.g., an opioid analgesic), which is resistant to crushing.

It is an object of certain embodiments of the present invention to provide a solid controlled release dosage form comprising an opioid analgesic, which is subject to less parenteral abuse than other dosage forms.

It is an object of certain embodiments of the present invention to provide a solid controlled release dosage form comprising an opioid analgesic, which is subject to less intranasal abuse than other dosage forms.

It is an object of certain embodiments of the present invention to provide a solid controlled release dosage form comprising an opioid analgesic, which is subject to less oral abuse than other dosage forms.

It is a further object of certain embodiments of the present invention to provide a solid controlled release dosage form comprising an opioid analgesic, which is subject to less diversion than other dosage forms.

It is a further object of certain embodiments of the present invention to provide a method of treating pain in human patients with a solid controlled release dosage form comprising an opioid analgesic while reducing the abuse potential of the dosage form.

It is a further object of certain embodiments of the present invention to treat a disease or condition (e.g., pain) by administering a solid controlled release dosage form as disclosed herein to a patient in need thereof.

It is a further object of certain embodiments of the present invention to provide a method of manufacturing an oral dosage form of an active agent (e.g., an opioid analgesic) as disclosed herein.

It is a further object of certain embodiments of the present invention to provide a use of a medicament (e.g., an opioid analgesic) in the manufacture of a dosage form for the treatment of a disease state (e.g., pain).

These objects and others are accomplished by the present invention, which in certain embodiments is directed to a solid controlled release dosage form comprising a core comprising a first portion of an active agent (e.g., an opioid analgesic) dispersed in a first matrix material; and a shell encasing the core and comprising a second portion of the active agent dispersed in a second matrix material; wherein the amount of active agent released from the dosage form is proportional within 20% to elapsed time from 8 to 24 hours, as measured by an in-vitro dissolution in a USP Apparatus 1 (basket) at 100 rpm in 900 ml simulated gastric fluid without enzymes (SGF) at 37° C.

In certain other embodiments, the amount of active agent released from the dosage form is proportional within 30% to elapsed time in at least one of (i) from 4 to 24 hours, (ii) from 8 to 24 hours, (iii) from 12 to 24 hours, (iv) from 18 to 24 hours, (v) from 4 to 8 hours, (vi) from 4 to 12 hours, (vii) from 4 to 18 hours, (viii) from 8 to 12 hours, (ix) from 8 to 18 hours, or (x) from 12 to 18 hours, as measured by an in-vitro dissolution in a USP Apparatus 1 (basket) at 100 rpm in 900 ml simulated gastric fluid without enzymes (SGF) at 37° C. In alternate embodiments, the amount of active agent released from the dosage form is proportional within 30% to elapsed time in all of (i) from 8 to 24 hours, (ii) from 8 to 12 hours, and (iii) from 8 to 18 hours, as measured by an in-vitro dissolution in a USP Apparatus 1 (basket) at 100 rpm in 900 ml simulated gastric fluid without enzymes (SGF) at 37° C.

In certain other embodiments, the amount of active agent released from the dosage form is proportional within 25% to elapsed time in at least one of (i) from 4 to 24 hours, (ii) from 8 to 24 hours, (iii) from 12 to 24 hours, (iv) from 18 to 24 hours, (v) from 4 to 8 hours, (vi) from 4 to 12 hours, (vii) from 4 to 18 hours, (viii) from 8 to 12 hours, (ix) from 8 to 18 hours, or (x) from 12 to 18 hours, as measured by an in-vitro dissolution in a USP Apparatus 1 (basket) at 100 rpm in 900 ml simulated gastric fluid without enzymes (SGF) at 37° C. In alternate embodiments, the amount of active agent released from the dosage form is proportional within 25% to elapsed time in all of (i) from 8 to 24 hours, (ii) from 8 to 12 hours, and (iii) from 8 to 18 hours, as measured by an in-vitro dissolution in a USP Apparatus 1 (basket) at 100 rpm in 900 ml simulated gastric fluid without enzymes (SGF) at 37° C.

In certain other embodiments, the amount of active agent released from the dosage form is proportional within 20% to elapsed time in at least one of (i) from 4 to 24 hours, (ii) from 8 to 24 hours, (iii) from 12 to 24 hours, (iv) from 18 to 24 hours, (v) from 4 to 8 hours, (vi) from 4 to 12 hours, (vii) from 4 to 18 hours, (viii) from 8 to 12 hours, (ix) from 8 to 18 hours, or (x) from 12 to 18 hours, as measured by an in-vitro dissolution in a USP Apparatus 1 (basket) at 100 rpm in 900 ml simulated gastric fluid without enzymes (SGF) at 37° C. In alternate embodiments, the amount of active agent released from the dosage form is proportional within 20% to elapsed time in all of (i) from 8 to 24 hours, (ii) from 8 to 12 hours, and (iii) from 8 to 18 hours, as measured by an in-vitro dissolution in a USP Apparatus 1 (basket) at 100 rpm in 900 ml simulated gastric fluid without enzymes (SGF) at 37° C.

In certain other embodiments, the amount of active agent released from the dosage form is proportional within 10% to elapsed time in at least one of (i) from 4 to 24 hours, (ii) from 8 to 24 hours, (iii) from 12 to 24 hours, (iv) from 18 to 24 hours, (v) from 4 to 8 hours, (vi) from 4 to 12 hours, (vii) from 4 to 18 hours, (viii) from 8 to 12 hours, (ix) from 8 to 18 hours, or (x) from 12 to 18 hours, as measured by an in-vitro dissolution in a USP Apparatus 1 (basket) at 100 rpm in 900 ml simulated gastric fluid without enzymes (SGF) at 37° C. In alternate embodiments, the amount of active agent released from the dosage form is proportional within 10% to elapsed time in all of (i) from 8 to 24 hours, (ii) from 8 to 12 hours, and (iii) from 8 to 18 hours, as measured by an in-vitro dissolution in a USP Apparatus 1 (basket) at 100 rpm in 900 ml simulated gastric fluid without enzymes (SGF) at 37° C.

In certain other embodiments, the amount of active agent released from the dosage form is proportional within 5% to elapsed time in at least one of (i) from 4 to 24 hours, (ii) from 8 to 24 hours, (iii) from 12 to 24 hours, (iv) from 18 to 24 hours, (v) from 4 to 8 hours, (vi) from 4 to 12 hours, (vii) from 4 to 18 hours, (viii) from 8 to 12 hours, (ix) from 8 to 18 hours, or (x) from 12 to 18 hours, as measured by an in-vitro dissolution in a USP Apparatus 1 (basket) at 100 rpm in 900 ml simulated gastric fluid without enzymes (SGF) at 37° C. In alternate embodiments, the amount of active agent released from the dosage form is proportional within 5% to elapsed time in all of (i) from 8 to 24 hours, (ii) from 8 to 12 hours, and (iii) from 8 to 18 hours, as measured by an in-vitro dissolution in a USP Apparatus 1 (basket) at 100 rpm in 900 ml simulated gastric fluid without enzymes (SGF) at 37° C.

In certain embodiments, the present invention is directed to a solid controlled release dosage form comprising a core comprising a first portion of an active agent (e.g., an opioid analgesic) dispersed in a first matrix material comprising polyethylene oxide; and a shell encasing the core and comprising a second portion of the active agent dispersed in a second matrix material comprising polyethylene oxide. In alternative embodiments, only the first matrix material comprises polyethylene oxide or only the second matrix material comprises polyethylene oxide.

In certain embodiments, the present invention is directed to a solid controlled release dosage form comprising a compressed core comprising a first portion of an active agent (e.g., an opioid analgesic) dispersed in a first matrix material comprising polyethylene oxide; and a compression coating encasing the core and comprising a second portion of the active agent dispersed in a second matrix material comprising polyethylene oxide.

In certain embodiments, the present invention is directed to a solid controlled release dosage form comprising a core comprising a first portion of an active agent (e.g., an opioid analgesic) dispersed in a first matrix material; and a shell encasing the core and comprising a second portion of the active agent dispersed in a second matrix material; wherein the amount of active agent released from the dosage form at 2 hours is less than about 25%; the amount of active agent released from the dosage form at 4 hours is from about 10% to about 30%; the amount of active agent released from the dosage form at 8 hours is from about 20% to about 60%; the amount of active agent released from the dosage form at 12 hours is from about 40% to about 90%; and the amount of active agent released from the dosage form at 18 hours is greater than about 70%; as measured by an in-vitro dissolution in a USP Apparatus 1 (basket) at 100 rpm in 900 ml simulated gastric fluid without enzymes (SGF) at 37° C.

In certain embodiments, the present invention is directed to a solid controlled release dosage form comprising a core comprising a first portion of an active agent (e.g., an opioid analgesic) dispersed in a first matrix material; and a shell encasing the core and comprising a second portion of the active agent dispersed in a second matrix material; wherein the amount of active agent released from the dosage form at 2 hours is less than about 20%; the amount of active agent released from the dosage form at 4 hours is from about 10% to about 30%; the amount of active agent released from the dosage form at 8 hours is from about 30% to about 60%; the amount of active agent released from the dosage form at 12 hours is from about 50% to about 90%; and the amount of active agent released from the dosage form at 18 hours is greater than about 80%; as measured by an in-vitro dissolution in a USP Apparatus 1 (basket) at 100 rpm in 900 ml simulated gastric fluid without enzymes (SGF) at 37° C.

In certain embodiments, the present invention is directed to a solid controlled release dosage form comprising a core comprising a first portion of an active agent (e.g., an opioid analgesic) dispersed in a first matrix material; and a shell encasing the core and comprising a second portion of the active agent dispersed in a second matrix material; wherein the amount of active agent released from the dosage form at 2 hours is less than about 15%; the amount of active agent released from the dosage form at 4 hours is from about 8% to about 20%; the amount of active agent released from the dosage form at 8 hours is from about 20% to about 50%; the amount of active agent released from the dosage form at 12 hours is from about 40% to about 70%; the amount of active agent released from the dosage form at 18 hours is greater than about 70%; and the amount of active agent released from the dosage form at 24 hours is greater than about 90%; as measured by an in-vitro dissolution in a USP Apparatus 1 (basket) at 100 rpm in 900 ml simulated gastric fluid without enzymes (SGF) at 37° C. In certain embodiments, the present invention is directed to a solid controlled release dosage form comprising a therapeutically effective amount of hydrocodone or a pharmaceutically acceptable salt thereof, and a controlled release excipient; wherein the amount of opioid analgesic released from the dosage form is proportional within 20% to elapsed time from 8 to 24 hours, as measured by an in-vitro dissolution in a USP Apparatus 1 (basket) at 100 rpm in 900 ml simulated gastric fluid without enzymes (SGF) at 37° C.; and the dosage form can be flattened without breaking, wherein the thickness of the dosage form after flattening corresponds to no more than about 20% of the thickness of the dosage form before flattening; and the amount of hydrocodone or salt thereof released at 0.5 hour from a flattened dosage form deviates no more than about 20% points from a non-flattened dosage form as measured by an in-vitro dissolution in a USP Apparatus 1 (basket) at 100 rpm in 900 ml simulated gastric fluid without enzymes (SGF) at 37° C.

In certain embodiment, the present invention is directed to a solid controlled release dosage form comprising a therapeutically effective amount of hydrocodone or a pharmaceutically acceptable salt thereof, and a controlled release excipient; wherein the amount of hydrocodone or salt thereof released from the dosage form at 2 hours is less than about 25%; the amount of hydrocodone or salt thereof released from the dosage form at 4 hours is from about 10% to about 30%; the amount of hydrocodone or salt thereof released from the dosage form at 8 hours is from about 20% to about 60%; the amount of hydrocodone or salt thereof released from the dosage form at 12 hours is from about 40% to about 90%; and the amount of hydrocodone or salt thereof released from the dosage form at 18 hours is greater than about 70%; as measured by an in-vitro dissolution in a USP Apparatus 1 (basket) at 100 rpm in 900 ml simulated gastric fluid without enzymes (SGF) at 37° C.; and the dosage form can be flattened without breaking, wherein the thickness of the dosage form after flattening corresponds to no more than about 20% of the thickness of the dosage form before flattening; and the amount of hydrocodone or salt thereof released at 0.5 hour from a flattened dosage form deviates no more than about 20% points from a non-flattened dosage form as measured by an in-vitro dissolution in a USP Apparatus 1 (basket) at 100 rpm in 900 ml simulated gastric fluid without enzymes (SGF) at 37° C.

In certain embodiments, the present invention is directed to a solid controlled release dosage form comprising a therapeutically effective amount of hydrocodone or a pharmaceutically acceptable salt thereof dispersed in a controlled release excipient; wherein the inner 60% of the dosage form contains at least 80% of the hydrocodone or salt thereof; wherein the amount of hydrocodone or salt thereof released from the dosage form is proportional within 20% to elapsed time from 8 to 24 hours, as measured by an in-vitro dissolution in a USP Apparatus 1 (basket) at 100 rpm in 900 ml simulated gastric fluid without enzymes (SGF) at 37° C.

In certain embodiments, the present invention is directed to a method of preparing a solid controlled release dosage form comprising preparing a core comprising a first portion of an active agent (e.g., an opioid analgesic) dispersed in a first matrix material; and encasing the core in a shell comprising a second portion of the active agent dispersed in a second matrix material; wherein the amount of active agent released from the dosage form is proportional within 20% to elapsed time from 8 to 24 hours, as measured by an in-vitro dissolution in a USP Apparatus 1 (basket) at 100 rpm in 900 ml simulated gastric fluid without enzymes (SGF) at 37° C.

In certain embodiments, the present invention is directed to a method of preparing a solid controlled release dosage form comprising preparing a core comprising a first portion of an active agent (e.g., an opioid analgesic) dispersed in a first matrix material comprising polyethylene oxide; and encasing the core in a shell comprising a second portion of the active agent dispersed in a second matrix material comprising polyethylene oxide. In alternative embodiments, corresponding dosage forms are prepared such that only the first matrix material comprises polyethylene oxide or only the second matrix material comprises polyethylene oxide.

In certain embodiments, the present invention is directed to a method of preparing a solid controlled release dosage form comprising preparing a compressed core comprising a first portion of an active agent (e.g., an opioid analgesic) dispersed in a first matrix material comprising polyethylene oxide; and encasing the core by compression coating a second portion of the active agent dispersed in a second matrix material comprising polyethylene oxide over the core. In alternative embodiments, corresponding compression coated dosage forms are prepared such that only the first matrix material comprises polyethylene oxide or only the second matrix material comprises polyethylene oxide.

In certain embodiments, the present invention is directed to a method of preparing a solid controlled release dosage form comprising preparing a core comprising a first portion of an active agent (e.g., an opioid analgesic) dispersed in a first matrix material; and encasing the core in a shell comprising a second portion of the active agent dispersed in a second matrix material over the core; wherein the amount of active agent released from the dosage form at 2 hours is less than about 25%; the amount of active agent released from the dosage form at 4 hours is from about 10% to about 30%; the amount of active agent released from the dosage form at 8 hours is from about 20% to about 60%; the amount of active agent released from the dosage form at 12 hours is from about 40% to about 90%; and the amount of active agent released from the dosage form at 18 hours is greater than about 70%, as measured by an in-vitro dissolution in a USP Apparatus 1 (basket) at 100 rpm in 900 ml simulated gastric fluid without enzymes (SGF) at 37° C.

In certain embodiments, the present invention is directed to a method of preparing a solid controlled release dosage form comprising combining a therapeutically effective amount of hydrocodone or a pharmaceutically acceptable salt thereof, and a controlled release excipient; wherein the amount of hydrocodone or salt thereof released from the dosage form at 2 hours is less than about 25%; the amount of hydrocodone or salt thereof released from the dosage form at 4 hours is from about 10% to about 30%; the amount of hydrocodone or salt thereof released from the dosage form at 8 hours is from about 20% to about 60%; the amount of hydrocodone or salt thereof released from the dosage form at 12 hours is from about 40% to about 90%; and the amount of hydrocodone or salt thereof released from the dosage form at 18 hours is greater than about 70%; as measured by an in-vitro dissolution in a USP Apparatus 1 (basket) at 100 rpm in 900 ml simulated gastric fluid without enzymes (SGF) at 37° C.; and the dosage form can be flattened without breaking, wherein the thickness of the dosage form after flattening corresponds to no more than about 20% of the thickness of the dosage form before flattening; and the amount of hydrocodone or salt thereof released at 0.5 hour from a flattened dosage form deviates no more than about 20% points from a non-flattened dosage form as measured by an in-vitro dissolution in a USP Apparatus 1 (basket) at 100 rpm in 900 ml simulated gastric fluid without enzymes (SGF) at 37° C.

In certain embodiment, the present invention is directed to a method of preparing a solid controlled release dosage form comprising combining a therapeutically effective amount of hydrocodone or a pharmaceutically acceptable salt thereof, and a controlled release excipient; wherein the amount of hydrocodone or salt thereof released from the dosage form is proportional within 20% to elapsed time, at any two time points from 8 to 24 hours, as measured by an in-vitro dissolution in a USP Apparatus 1 (basket) at 100 rpm in 900 ml simulated gastric fluid without enzymes (SGF) at 37° C.; and the dosage form can be flattened without breaking, wherein the thickness of the dosage form after flattening corresponds to no more than about 20% of the thickness of the dosage form before flattening; and the amount of hydrocodone or salt thereof released at 0.5 hour from a flattened dosage form deviates no more than about 20% points from a non-flattened dosage form as measured by an in-vitro dissolution in a USP Apparatus 1 (basket) at 100 rpm in 900 ml simulated gastric fluid without enzymes (SGF) at 37° C.

In certain embodiments, the present invention is directed to a method of preparing a solid controlled release dosage form comprising dispersing a therapeutically effective amount of hydrocodone or a pharmaceutically acceptable salt thereof in a controlled release excipient; wherein the inner 60% of the dosage form contains at least 80% of the hydrocodone or salt thereof; wherein the amount of hydrocodone or salt thereof released from the dosage form is proportional within 20% to elapsed time from 8 to 24 hours, as measured by an in-vitro dissolution in a USP Apparatus 1 (basket) at 100 rpm in 900 ml simulated gastric fluid without enzymes (SGF) at 37° C.

In certain embodiments, the present invention is directed to a method of treating pain in a patient or subject comprising administering a solid controlled release dosage form comprising an opioid analgesic as disclosed herein.

In preferred embodiments, the present invention is directed to a dosage form of the present invention which exhibits a substantially zero-order release rate after administration to a patient or subject.

The term "zero-order release rate" refers to the rate of active agent release from a dosage form which is independent of remaining active agent concentration in the dosage form, such that the rate is relatively constant over a period of time. A dosage form exhibiting zero order release rate would exhibit a relatively straight line in a graphical representation of percent active agent released versus time. In certain embodiments of the present invention, substantial zero order release is defined as a dosage form having an amount of active agent released which is proportional within 20% to elapsed time from 8 to 24 hours or 4 to 12 hours, as measured by an in-vitro dissolution in a USP Apparatus 1 (basket) at 100 rpm in 900 ml simulated gastric fluid without enzymes (SGF) at 37° C. For example, an amount released from a dosage form in-vitro at 8 hours of 20%, and an amount released at 24 hours of 60% (±12) would literally meet the definition of proportional within 20% to elapsed time from 8 to 24 hours. This is demonstrated by the latter elapsed time (24 hours) and the latter release (60%) being the same multiple (3) of the former time (8 hours) and the former release (20%). To meet the definition of proportional within 20% to elapsed time from 8 to 24 hours (or any other time period) it is only necessary to consider the endpoints of the numerical values, although the definition does not preclude that other time points within the endpoints may be proportional as well.

In other embodiments of the present invention, substantial zero order release is defined as a dosage form wherein the amount of active agent released at 2 hours is less than about 25%; the amount of active agent released from the dosage form at 4 hours is from about 10% to about 30%; the amount of active agent released from the dosage form at 8 hours is from about 20% to about 60%; the amount of active agent released from the dosage form at 12 hours is from about 40% to about 90%; and the amount of active agent released from the dosage form at 18 hours is greater than about 70%; as measured by an in-vitro dissolution in a USP Apparatus 1 (basket) at 100 rpm in 900 ml simulated gastric fluid without enzymes (SGF) at 37° C.

The term "polyethylene oxide" is defined for purposes of the present invention as a composition of polyethylene oxide (PEO) having a molecular weight of at least 25,000, measured as is conventional in the art, and preferably having a molecular weight of at least 100,000. Compositions with lower molecular weight are usually referred to as polyethylene glycols.

The term "high molecular weight polyethylene oxide (PEO)" is defined for proposes of the present invention as having an approximate molecular weight of at least 1,000,000, based on rheological measurements.

The term "low molecular weight polyethylene oxide (PEO)" is defined for purposes of the present invention as having an approximate molecular weight of less than 1,000,000, based on rheological measurements.

The term "direct compression" is defined for purposes of the present invention as referring to a process wherein the dosage form is made by a process comprising the steps of blending the ingredients and compressing the blend to form the dosage form, e.g., by using a diffusion blend and/or convection mixing process (e.g., Guidance for Industry, SUPAC-IR/MR: Immediate Release and Modified Release Solid Oral Dosage Forms, Manufacturing Equipment Addendum).

The term "flattening" and related terms as used in the context of flattening a dosage form in accordance with the present invention means that the dosage form is subjected to force applied from a direction substantially in line with the smallest diameter (i.e., the thickness) of the dosage form when the shape is other than spherical, and from any direction when the dosage form shape is spherical.

The term "resistant to crushing" is defined for the purposes of certain embodiments of the present invention as referring to dosage forms that can at least be flattened with a bench press as described herein without breaking.

For purposes of the present invention, the term "opioid analgesic" means one or more compounds selected from base opioid agonists, mixed opioid agonist-antagonists, partial opioid agonists, pharmaceutically acceptable salts, complexes, stereoisomers, ethers, esters, hydrates and solvates thereof and mixtures thereof.

The term "simulated gastric fluid" or "SGF" used herein refers to an aqueous solution utilized in dissolution testing to mimic the conditions of the stomach, e.g., a solution of 0.1 N HCl.

The term "percentage points" in the context of, e.g., "the amount of active agent released at 0.5 hour from a flattened dosage form deviates no more than about 20% points from a non-flattened dosage form" means that the difference in the % release prior to flattening and the % release after flattening is no more than 20 (i.e., 20 or less). For example, 60% release from a flattened dosage form is no more than about 20% points from the 40% release of a non-flattened dosage form.

The term "percentage" or the use of "%" without reference to "percentage (or %) points" is the ordinary meaning of percent. For example, 48% release is within 20% of 60% release, whereas 40% would not literally be within 20% of 60% release.

The term "patient" means a subject (preferably a human) who has presented a clinical manifestation of a particular symptom or symptoms suggesting the need for treatment, who is treated preventatively or prophylactically for a condition, or who has been diagnosed with a condition to be treated.

The term "subject" is inclusive of the definition of the term "patient" and inclusive of the term "healthy subject" (i.e., an individual (e.g., a human) who is entirely normal in all respects or with respect to a particular condition.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" refers to a carbon atom to which four different groups are attached.

The term "enantiomer" or "enantiomeric" refers to a molecule that is nonsuperimposable on its mirror image and hence optically active wherein the enantiomer rotates the plane of polarized light in one direction and its mirror image rotates the plane of polarized light in the opposite direction.

The term "racemic" refers to a mixture of enantiomers.

The term "resolution" refers to the separation or concentration or depletion of one of the two enantiomeric forms of a molecule.

"Hydrocodone" is defined for purposes of the invention as including hydrocodone free base, as well as pharmaceutically acceptable salts, complexes, stereoisomers, ethers, esters, hydrates and solvates thereof and mixtures thereof The term "USP Paddle or Basket Method" is the Paddle and Basket Method described, e.g., in U.S. Pharmacopoeia XII (1990).

The term "pH-dependent" for purposes of the present invention is defined as having characteristics (e.g., dissolution) which vary according to environmental pH.

The term "pH-independent" for purposes of the present invention is defined as having characteristics (e.g., dissolution) which are substantially unaffected by pH.

The term "bioavailability" is defined for purposes of the present invention as the relevant extent to which the drug (e.g., hydrocodone) is absorbed from the unit dosage forms. Bioavailability is also referred to as AUC (i.e., area under the plasma concentration/time curve).

The term "controlled-release", "extended-release" or "sustained release" are interchangeable and are defined for purposes of the present invention as the release of the drug (e.g., hydrocodone) at such a rate that blood (e.g., plasma) concentrations are maintained within the therapeutic range but below toxic concentrations over a period of time of at least about 12 hours or longer, or at least 24 hours or longer. Preferably, a controlled release dosage form can provide once daily or twice daily dosing.

The term "$C_{max}$" denotes the maximum plasma concentration obtained during the dosing interval.

The term "$C_{24}$" as it is used herein is the plasma concentration of the drug at 24 hours after administration.

The term "$T_{max}$" denotes the time to maximum plasma concentration ($C_{max}$).

The term "$C_{24}/C_{max}$ ratio" is defined for purposes of the present invention as the ratio of the plasma concentration of the drug at 24 hours after administration to the highest plasma concentration of the drug attained within the dosing interval.

The term "$T_{lag}$" denotes the time point immediately prior to the first measurable plasma concentration.

The term "$T_{1/2}$" denotes the plasma half-life of the terminal phase. This is the time it takes for any concentration in the terminal phase to decrease by half. The term "minimum effective analgesic concentration" or "MEAC" with respect to concentrations of opioids such as hydrocodone is very difficult to quantify. However, there is generally a minimally effective analgesic concentration of plasma hydrocodone below which no analgesia is provided. While there is an indirect relationship between, e.g., plasma hydrocodone levels and analgesia, higher and prolonged plasma levels are generally associated with superior pain relief There is a delay (or hysteresis) between the time of peak plasma hydrocodone-levels and the time of peak drug effects. This holds true for the treatment of pain with opioid analgesics in general.

For purposes of the present invention, unless further specified, the term "a patient" or "a subject" means that the discussion (or claim) is directed to the pharmacokinetic parameters of an individual patient or subject.

The term "population of patients" or "population of subjects" or "population of healthy subjects" means that the discussion (or claim) is directed to the mean pharmacokinetic parameters of at least two patients, subjects, or healthy subjects; at least six patients, subjects or healthy subjects; or at least twelve patients, subjects or healthy subjects.

For purposes of the present invention, the controlled release formulations disclosed herein are preferably dose proportional. In dose proportional formulations, the pharmacokinetic parameters (e.g., AUC and $C_{max}$) and/or in-vitro release increase linearly from one dosage strength to another. Therefore, the pharmacokinetic and in-vitro parameters of a particular dose can be inferred from the parameters of a different dose of the same formulation.

The term "first administration" means a single dose of the present invention at the initiation of therapy to an individual subject, patient, or healthy subject or a subject population, patient population, or healthy subject population.

The term "steady state" means that the amount of the drug reaching the system is approximately the same as the amount of the drug leaving the system. Thus, at "steady-state", the patient's body eliminates the drug at approximately the same rate that the drug becomes available to the patient's system through absorption into the blood stream.

DETAILED DESCRIPTION

Figure 1:
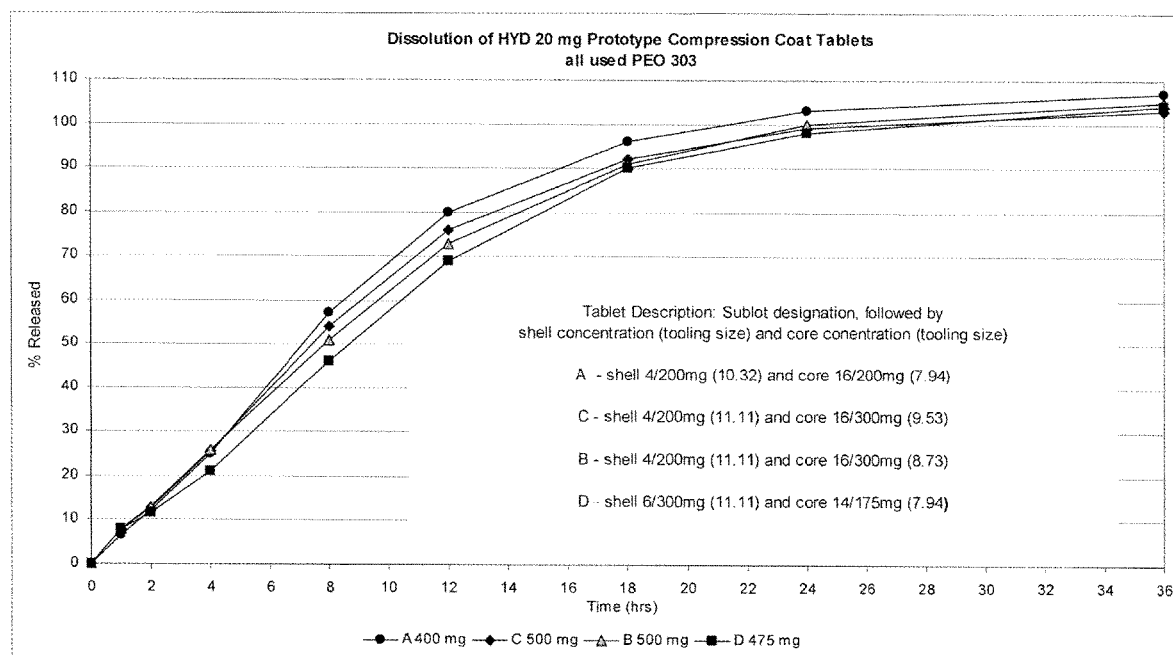
FIG. 1 is a graph that depicts the dissolution of the compositions of Examples 1-4.

The present invention is directed to controlled release pharmaceutical formulations that in certain embodiments comprise a higher concentration of drug in an inner region of the dosage form as compared to an outer region. Preferably, the inner and outer regions are configured as an inner core (e.g., a compressed tablet) and a shell encasing the core (e.g., a compression coating). The active agent can be contained solely in the core or contained in both the core and the shell. In preferred embodiments, the release of the active agent from the dosage form is substantially zero order, which provides dosing certainty and reduced plasma fluctuations as compared to alternative treatments (e.g., immediate release dosage forms).

The dosage forms of the present invention are preferably tamper resistant as they are difficult to crush or grind (e.g., in accordance with the flattening criteria disclosed herein). This characteristic makes them especially suitable for controlled release opioid analgesic products that have a large dose of opioid analgesic intended to be released over a period of time from each dosage unit. Drug abusers typically may take a controlled-release product and crush, shear, grind, chew, dissolve, heat, extract or otherwise damage the product so that a large portion or the full contents of the dosage form becomes available for immediate absorption by injection, inhalation, and/or oral consumption.

The shell of the dosage form of the present invention is preferably difficult to physically separate from the core. This is particularly useful in embodiments that have an increased amount of active agent in the core as compared to the shell, as abusers will have difficulty in accessing the greater drug payload of the core.

In certain embodiments, the present invention is directed to a solid controlled release dosage form comprising: a core comprising a first portion of an opioid analgesic dispersed in a first matrix material; and a shell encasing the core and comprising a second portion of the opioid analgesic dispersed in a second matrix material.

The core of the dosage form can be formed, e.g., by direct compression, extrusion or molding. Preferably, the inner core provides a controlled release excipient and is in the form of a compressed tablet.

The shell of the dosage form can be formed, e.g., by compression coating, molding, spraying one or more layers onto the core, dipping one or more layers onto the core or a combination thereof. Preferably, the shell contains a controlled release excipient and is a compression coating.

In preferred embodiments, the weight ratio of the core to the shell of the dosage forms described herein is from about 1:0.5 to about 1:5; from about 1:0.5 to about 1:2; from about 1:0.6 to about 1:1.5; or from about 1:0.8 to about 1:1.2.

In preferred embodiments, the core and the shell are visually indistinguishable (e.g., by color) and there is not a clear demarcation between each component. This contributes to tamper resistance of the dosage form by hindering efforts to access the core, which in certain embodiments will contain the bulk of the active agent. One measurement that can be utilized in order to evaluate the color of the shell and the core is CIE L*A*B* value. Preferably, the CIE L*A*B* value of the core and the shell are within 10% of each other. Another measurement to evaluate color is the use of a RYB or RGB color wheel, where the core and shell preferably correspond to the same hue or adjacent hues.

In certain embodiments, the first matrix material comprises PEO. In other embodiments, the second matrix material comprises PEO. In yet other embodiments, the first matrix material comprises PEO and the second matrix material comprises PEO. Preferably, polyethylene oxide is contained in both components. In such embodiments, the molecular weight of the PEO in the first matrix material is the same or different than the average molecular weight in the second matrix material. In certain embodiments, molecular weight of the PEO contained in both components is within 20%, within 10% or within 5% of each other.

In preferred embodiments of the present invention, when polyethylene oxide is present in both the first and second matrices, the molecular weight of the polyethylene oxide used in the first matrix (in the core) is lower than the molecular weight of the polyethylene oxide used in the second matrix material (in the shell). For example, in preferred embodiments, the polyethylene oxide in the first matrix material may have a molecular weight from about 300,000 to about and the polyethylene oxide in the second matrix material may have a molecular weight from about 1,000,000 to about 10,000,000. In other preferred embodiments, the polyethylene oxide in the first matrix material may have a molecular weight from about 300,000 to about 3,000,000 and the polyethylene oxide in the second matrix material may have a molecular weight from about 4,000,000 to about 10,000,000. In other preferred embodiments, the polyethylene oxide in the first matrix material may have a molecular weight from about 500,000 to about 1,000,000 and the polyethylene oxide in the second matrix material may have a molecular weight from about 6,000,000 to about 8,000,000.

In certain embodiments, the active agent (e.g., opioid analgesic) in the first portion (in the core) is the same as the active agent in the second portion (in the shell). In other embodiments, the active agent in the first portion is different than the active agent in the second portion.

In certain embodiments, the ratio of active agent (e.g., opioid analgesic) in the core to the ratio of active agent in the shell is from about 1:1 to about 10:1; from about 2:1 to about 8:1; from about 2:1 to about 5:1 or about 4:1.

In certain embodiments, the weight ratio of the first portion of active agent (e.g., opioid analgesic) to polyethylene oxide in the first matrix material is from about 1:0.25 to about 1:30; from about 1:0.5 to about 1:100; from about 1:0.5 to about 1:20; from about 1:1 to about 1:10; from about 1:15 to about 1:20; from about 1:1.5 to about 1:4; about 1:18 or about 1:2.

In alternative embodiments, the weight ratio of the second portion of active agent (e.g., opioid analgesic) to polyethylene oxide in the second matrix material is from about 1:1 to about 1:200; from about 1:1 to about 1:125; from about 1:2 to about 1:100; from about 1:5 to about 1:50; from about 1:12 to about 1:25; about 1:98 or about 1:15.

In certain embodiments, the amount of active agent (e.g., opioid analgesic) released from the dosage form is proportional within 20%, or within 10%, or within 5% to elapsed time from 8 to 24 hours, as measured by an in-vitro dissolution in a USP Apparatus 1 (basket) at 100 rpm in 900 ml simulated gastric fluid without enzymes (SGF) at 37° C.

In certain embodiments, the amount of active agent (e.g., opioid analgesic) released from the dosage form is proportional within 20%, or within 10%, or within 5% to elapsed time from 8 to 18 hours, as measured by an in-vitro dissolution in a USP Apparatus 1 (basket) at 100 rpm in 900 ml simulated gastric fluid without enzymes (SGF) at 37° C.

In certain embodiments, the amount of active agent (e.g., opioid analgesic) released from the dosage form is proportional within 20%, or within 10%, or within 5% to elapsed time from 8 to 12 hours, as measured by an in-vitro dissolution in a USP Apparatus 1 (basket) at 100 rpm in 900 ml simulated gastric fluid without enzymes (SGF) at 37° C.

In certain embodiments, the amount of active agent (e.g., opioid analgesic) released from the dosage form is proportional within 20%, or within 10%, or within 5% to elapsed time from 12 to 24 hours, as measured by an in-vitro dissolution in a USP Apparatus 1 (basket) at 100 rpm in 900 ml simulated gastric fluid without enzymes (SGF) at 37° C.

In certain embodiments, the amount of active agent (e.g., opioid analgesic) released from the dosage form is proportional within 20%, or within 10%, or within 5% to elapsed time from 12 to 18 hours, as measured by an in-vitro dissolution in a USP Apparatus 1 (basket) at 100 rpm in 900 ml simulated gastric fluid without enzymes (SGF) at 37° C.

In certain embodiments, the amount of active agent (e.g., opioid analgesic) released from the dosage form is proportional within 20%, or within 10%, or within 5% to elapsed time from 4 to 20 hours, as measured by an in-vitro dissolution in a USP Apparatus 1 (basket) at 100 rpm in 900 ml simulated gastric fluid without enzymes (SGF) at 37° C.

In certain embodiments, the amount of active agent (e.g., opioid analgesic) released from the dosage form is proportional within 20%, or within 10%, or within 5% to elapsed time from 4 to 15 hours, as measured by an in-vitro dissolution in a USP Apparatus 1 (basket) at 100 rpm in 900 ml simulated gastric fluid without enzymes (SGF) at 37° C.

In certain embodiments, the amount of active agent (e.g., opioid analgesic) released from the dosage form is proportional within 20%, or within 10%, or within 5% to elapsed time from 4 to 10 hours, as measured by an in-vitro dissolution in a USP Apparatus 1 (basket) at 100 rpm in 900 ml simulated gastric fluid without enzymes (SGF) at 37° C.

In certain embodiments, the amount of active agent (e.g., opioid analgesic) released from the dosage form is proportional within 20%, or within 10%, or within 5% to elapsed time from 8 to 20 hours, as measured by an in-vitro dissolution in a USP Apparatus 1 (basket) at 100 rpm in 900 ml simulated gastric fluid without enzymes (SGF) at 37° C.

In certain embodiments, the amount of active agent (e.g., opioid analgesic) released from the dosage form is proportional within 20%, or within 10%, or within 5% to elapsed time from 10 to 15 hours, as measured by an in-vitro dissolution in a USP Apparatus 1 (basket) at 100 rpm in 900 ml simulated gastric fluid without enzymes (SGF) at 37° C.

In certain embodiments, the amount of active agent (e.g., opioid analgesic) released at 2 hours is less than about 25%; the amount of active agent released from the dosage form at 4 hours is from about 10% to about 30%; the amount of active agent released from the dosage form at 8 hours is from about 20% to about 60%; the amount of active agent released from the dosage form at 12 hours is from about 40% to about 90%; and the amount of active agent released from the dosage form at 18 hours is greater than about 70%; as measured by an in-vitro dissolution in a USP Apparatus 1 (basket) at 100 rpm in 900 ml simulated gastric fluid without enzymes (SGF) at 37° C.

In certain embodiments, the amount of active agent (e.g., opioid analgesic) released at 2 hours is less than about 15%; the amount of active agent released from the dosage form at 4 hours is from about 10% to about 20%; the amount of active agent released from the dosage form at 8 hours is from about 30% to about 45%; the amount of active agent released from the dosage form at 12 hours is from about 50% to about 70%; and the amount of active agent released from the dosage form at 18 hours is greater than about 90%; as measured by an in-vitro dissolution in a USP Apparatus 1 (basket) at 100 rpm in 900 ml simulated gastric fluid without enzymes (SGF) at 37° C.

In certain embodiments, the amount of active agent (e.g., opioid analgesic) released at 2 hours is less than about 10%; the amount of active agent released from the dosage form at 4 hours is from about 20% to about 30%; the amount of active agent released from the dosage form at 8 hours is from about 45% to about 60%; the amount of active agent released from the dosage form at 12 hours is from about 70% to about 90%; and the amount of active agent released from the dosage form at 18 hours is greater than about 95%; as measured by an in-vitro dissolution in a USP Apparatus 1 (basket) at 100 rpm in 900 ml simulated gastric fluid without enzymes (SGF) at 37° C.

In certain embodiments, the amount of active agent (e.g., opioid analgesic) released from the dosage form is proportional within 20% to elapsed time from 8 to 24 hours, as measured by an in-vitro dissolution in a USP Apparatus 1 (basket) at 100 rpm in 900 ml simulated gastric fluid without enzymes (SGF) at 37° C. and at least one of the following is exhibited: (i) the amount of opioid analgesic released at 2 hours is less than about 20%, (ii) the amount of opioid analgesic released at 4 hours is from about 10% to about 30%, (iii) the amount of opioid analgesic released at 8 hours is from about 30% to about 60%, (iv) the amount of opioid analgesic released at 12 hours is from about 50% to about 90%, or (v) the amount of opioid analgesic released at 18 hours is greater than about 80%.

In certain embodiments, the amount of active agent (e.g., opioid analgesic) released from the dosage form is proportional within 20% to elapsed time from 8 to 24 hours, as measured by an in-vitro dissolution in a USP Apparatus 1 (basket) at 100 rpm in 900 ml simulated gastric fluid without enzymes (SGF) at 37° C. and at least one of the following is exhibited: (i) the amount of opioid analgesic released at 2 hours is less than about 15%, (ii) the amount of opioid analgesic released at 4 hours is from about 10% to about 20%, (iii) the amount of opioid analgesic released at 8 hours is from about 30% to about 45%, (iv) the amount of opioid analgesic released at 12 hours is from about 50% to about 70%, or (v) the amount of opioid analgesic released at 18 hours is greater than about 90%.

In certain embodiments, the amount of active agent (e.g., opioid analgesic) released from the dosage form is proportional within 20% to elapsed time from 8 to 24 hours, as measured by an in-vitro dissolution in a USP Apparatus 1 (basket) at 100 rpm in 900 ml simulated gastric fluid without enzymes (SGF) at 37° C. and at least one of the following is exhibited: (i) the amount of opioid analgesic released at 2 hours is less than about 10%, (ii) the amount of opioid analgesic released at 4 hours is from about 20% to about 30%, (iii) the amount of opioid analgesic released at 8 hours is from about 45% to about 60%, (iv) the amount of opioid analgesic released at 12 hours is from about 70% to about 90%, or (v) the amount of opioid analgesic released at 18 hours is greater than about 95%.

In certain embodiments, the amount of active agent (e.g., opioid analgesic) released from the dosage form is proportional within 20% to elapsed time from 8 to 24 hours, as measured by an in-vitro dissolution in a USP Apparatus 1 (basket) at 100 rpm in 900 ml simulated gastric fluid without enzymes (SGF) at 37° C. and at least one of the following is exhibited: (i) the amount of opioid analgesic released at 2 hours is less than about 15%, (ii) the amount of opioid analgesic released at 4 hours is from about 8% to about 20%, (iii) the amount of opioid analgesic released at 8 hours is from about 20% to about 50%, (iv) the amount of opioid analgesic released at 12 hours is from about 40% to about 70%, (v) the amount of opioid analgesic released at 18 hours is greater than about 70% or (vi) the amount of opiid analgesic released from the dosage form at 24 hours is greater than about 90%.

Dosage Forms

In certain embodiments, the core may be prepared by dry blending a controlled release material, an active agent, and optionally other excipients, followed by granulating the mixture until proper granulation is obtained. The process can be performed by dry or wet granulation methods. Typically with a wet granulation, the wet granules are dried in a fluid bed dryer, and sifted and ground to appropriate size. Lubricating agents are typically mixed with the granulation to obtain the final core formulation.

A non-limiting list of suitable controlled release materials which may be selected for inclusion in a formulation according to the present invention includes hydrophilic and hydrophobic materials such as sustained release polymers, gums, acrylic resins, protein-derived materials, waxes, shellacs, and oils such as hydrogenated castor oil and hydrogenated vegetable oil. More specifically, the controlled release materials can be, e.g., alkylcelluloses such as ethylcellulose, acrylic and methacrylic acid polymers and copolymers, and cellulose ethers, such as hydroxyalkylcelluloses (e.g., hydroxypropylmethylcellulose) and carboxyalkylcelluloses. Waxes include, e.g., natural and synthetic waxes, fatty acids, fatty alcohols, and mixtures of the same (e.g., beeswax, carnauba wax, stearic acid and stearyl alcohol). Certain embodiments utilize mixtures of two or more of the foregoing controlled release materials in the matrix of the core. However, any pharmaceutically acceptable hydrophobic or hydrophilic controlled release material which is capable of imparting controlled release of the active agent may be used in accordance with the present invention.

The cores may also contain suitable quantities of additional excipients, e.g., lubricants, binders, granulating aids, diluents, colorants, flavorants (e.g., bittering agents) and glidants, all of which are conventional in the pharmaceutical art.

Specific examples of pharmaceutically acceptable diluents and excipients that may be used in formulating the cores are described in the Handbook of Pharmaceutical Excipients, American Pharmaceutical Association (1986), incorporated by reference herein.

In preferred embodiments, matrices of the dosage forms of the present invention incorporate polyethylene oxide (e.g., high and/or low molecular weight PEO).

Polyethylene oxide is considered to have an approximate molecular weight of 1,000,000 when a 2% (by wt) aqueous solution of the PEO using a Brookfield viscometer Model RVF, spindle No. 1, at 10 rpm, at 25° C. shows a viscosity range of 400 to 800 mPa-s (cP).

Polyethylene oxide is considered to have an approximate molecular weight of 2,000,000 when a 2% (by wt) aqueous solution of the PEO using a Brookfield viscometer Model RVF, spindle No. 3, at 10 rpm, at 25° C. shows a viscosity range of 2000 to 4000 mPa-s (cP).

Polyethylene oxide is considered to have an approximate molecular weight of 4,000,000 when a 1% (by wt) aqueous solution of the polyethylene oxide using a Brookfield viscometer Model RVF, spindle No. 2, at 2 rpm, at 25° C. shows a viscosity range of 1650 to 5500 mPa-s (cP).

Polyethylene oxide is considered to have an approximate molecular weight of 5,000,000 when a 1% (by wt) aqueous solution of the polyethylene oxide using a Brookfield viscometer Model RVF, spindle No. 2, at 2 rpm, at 25° C. shows a viscosity range of 5500 to 7500 mPa-s (cP).

Polyethylene oxide is considered to have an approximate molecular weight of 7,000,000 when a 1% (by wt) aqueous solution of the polyethylene oxide using a Brookfield viscometer Model RVF, spindle No. 2, at 2 rpm, at 25° C. shows a viscosity range of 7500 to 10,000 mPa-s (cP).

Polyethylene oxide is considered to have an approximate molecular weight of 8,000,000 when a 1% (by wt) aqueous solution of the polyethylene oxide using a Brookfield viscometer Model RVF, spindle No. 2, at 2 rpm, at 25° C. shows a viscosity range of 10,000 to 15,000 mPa-s (cP).

Regarding the lower molecular weight polyethylene oxides, polyethylene oxide is considered to have an approximate molecular weight of 100,000 when a 5% (by wt) aqueous solution of the polyethylene oxide using a Brookfield viscometer Model RVT, spindle No. 1, at 50 rpm, at 25° C. shows a viscosity range of 30 to 50 mPa-s (cP).

Polyethylene oxide is considered to have an approximate molecular weight of 900,000 when a 5% (by wt) aqueous solution of the polyethylene oxide using a Brookfield viscometer Model RVF, spindle No. 2, at 2 rpm, at 25° C. shows a viscosity range of 8800 to 17,600 mPa-s (cP).

Compression Coated Dosage Forms

In embodiments utilizing compression coating, it is preferred that all or part of the pharmaceutically acceptable excipient(s) in the coating should impart sufficient compressibility to provide a pharmaceutically acceptable product. The compression coating onto the pre-formed core is dependent in part on the individual characteristics of the selected excipients and the active agent, e.g., in terms of polymer solubility, flowability, glass transition temperature, etc.

Compression coated dosage forms can be prepared, e.g., by utilizing a pre-manufactured core or preparing a core (e.g., by compression) prior to the coating. The inner core can be prepared by wet or dry granulating active agent together with the pharmaceutically acceptable excipients; followed by drying and milling as necessary to obtain a granulate; adding optional extragranular excipients and/or active agent with appropriate blending; adding a lubricant as needed; and compressing the granulate with a tablet press. The resultant compressed core can be optionally coated with a functional coating or film coating prior to compression coating.

The blend for compression coating can be prepared by a similar process as the blend for the core utilizing any of the controlled release materials disclosed above. Preferably, the compression coating includes polyethylene oxide. The blend can be coated onto the core by compression. The compression of the core and/or the coating can utilize a Killion or Fette rotary press at a compression force, e.g., from about 1 to about 20 kilonewtons.

In certain embodiments, a Manesty Dry-Cota press (e.g., Model 900) can be utilized. This apparatus consists of two side by side interconnected tablet presses where the core is made on one press and then mechanically transferred to the next press for compression coating. Each press has an independent powder feed mechanism so that the core blend is loaded on one machine, and the coating blend is loaded on the other machine. Mechanical transfer arms rotate between the machines to remove cores from the core press and transfer them to the coating press. Other presses which may be used to prepare the dosage forms of the present invention include Elizabeth Hata HT-AP44-MSU-C; Killian RLUD; and Fette PT 4090, each of which has a dual feed system for coating blend and pre-made cores. Utilizing these presses allows multiple compression coating-layers to be achieved by recycling tablets that have already been compression-coated. All of these presses have mechanisms to center the tablet within the coating blend both vertically and radially.

In certain embodiments, the compression coating is not applied at the same thickness at all points around the inner core, but instead is applied at different thicknesses around the inner core. Thinner areas of coating will produce areas of the compressed dosage form that will release drug from the inner core sooner than other areas. This may be simply accomplished, e.g., by having the core to which the compression coating is being applied not being centered in the press at the time of coating.

In certain embodiments, the compression coated dosage form can be further overcoated with a hydrophobic or enteric coating material. In other embodiments, the compression coated dosage forms can be coated with a hydrophilic coating in addition to or instead of the hydrophobic or enteric coating.

In still further embodiments, an optional coat (e.g., hydrophobic, hydrophilic or enteric) may be alternatively or additionally applied as an intermediate layer between the core and the compression coating.

Active Agents

Opioid analgesics useful in the present invention include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, etorphine, dihydroetorphine, fentanyl and derivatives, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propoxyphene, sufentanil, tilidine, tramadol, pharmaceutically acceptable salts, complexes (e.g., with a cyclodextrin), stereoisomers, ethers, esters, hydrates, solvates, and mixtures thereof.

Preferably, the opioid analgesic is selected from the group consisting of codeine, hydrocodone, hydromorphone, morphine, oxycodone, oxymorphone, tramadol, pharmaceutically acceptable salts, complexes, stereoisomers, ethers, esters, hydrates, solvates, and mixtures thereof.

In certain embodiments, the opioid analgesic is selected from the group consisting of hydrocodone, pharmaceutically acceptable salts, complexes, stereoisomers, ethers, esters, hydrates, solvates, and mixtures thereof. Preferably, the opioid analgesic is hydrocodone bitartrate.

The opioids used according to the present invention may contain one or more asymmetric centers and may give rise to enantiomers, diastereomers, or other stereoisomeric forms. The present invention is meant to encompass the use of all such possible forms as well as their racemic and resolved forms and compositions thereof. When the compounds described herein contain olefinic double bonds or other centers of geometric asymmetry, it is intended to include both E and Z geometric isomers. All tautomers are intended to be encompassed by the present invention as well.

Pharmaceutically acceptable salts include, but are not limited to, inorganic acid salts such as hydrochloride, hydrobromide, sulfate, phosphate and the like; organic acid salts such as formate, acetate, trifluoroacetate, maleate, tartrate and the like; sulfonates such as methanesulfonate, benzenesulfonate, p-toluenesulfonate, and the like; amino acid salts such as arginate, asparaginate, glutamate and the like; metal salts such as sodium salt, potassium salt, cesium salt and the like; alkaline earth metals such as calcium salt, magnesium salt and the like; and organic amine salts such as triethylamine salt, pyridine salt, picoline salt, ethanolamine salt, triethanolamine salt, dicyclohexylamine salt, N,N'-dibenzylethylenediamine salt and the like.

Additionally, active agents other than opioid analgesics that are potentially subject to abuse may be used in accordance with the present invention. Such agents include, e.g., tranquilizers, CNS depressants, CNS stimulants, sedatives, hypnotics, stimulants (including appetite suppressants such as phenylpropanolamine), and cannabinoids, among others. More specifically, the active agent can be selected from barbiturates such as phenobarbital, secobarbital, pentobarbital, butabarbital, talbutal, aprobarbital, mephobarbital, butalbital, pharmaceutically acceptable salts thereof, and the like; benzodiazepines such as diazepam, chlordiazepoxide, alprazolam, triazolam, estazolam, clonazepam, flunitrazepam, pharmaceutically acceptable salts thereof, and the like; stimulants such as gamma-hydroxybutyrate, dextroamphetamine, methylphenidate, sibutramine, methylenedioxyrnethamphetamine, pharmaceutically acceptable salts thereof, and the like; other agents such as marinol, meprobamate and carisoprodol; and all pharmaceutically acceptable salts, complexes, stereoisomers, ethers, esters, hydrates, solvates, and mixtures thereof.

In further embodiments, other therapeutically active agents may be used in accordance with the present invention, either alone or in combination with opioids. Examples of such therapeutically active agents include antihistamines (e.g., dimenhydrinate, diphenhydramine, chlorpheniramine and dexchlorpheniramine maleate), non-steroidal anti-inflammatory agents (e.g., naproxen, diclofenac, indomethacin, ibuprofen, sulindac, Cox-2 inhibitors), acetaminophen, anti-emetics (e.g., metoclopramide, methylnaltrexone), anti-epileptics (e.g., phenyloin, meprobmate and nitrazepam), vasodilators (e.g., nifedipine, papaverine, diltiazem and nicardipine), anti-tussive agents and expectorants, anti-asthmatics (e.g. theophylline), antacids, anti-spasmodics (e.g., atropine, scopolamine), antidiabetics (e.g., insulin), diuretics (e.g., ethacrynic acid, bendrofluthiazide), anti-hypotensives (e.g., propranolol, clonidine), antihypertensives (e.g., clonidine, methyldopa), bronchodilators (e.g., albuterol), steroids (e.g., hydrocortisone, triamcinolone, prednisone), antibiotics (e.g., tetracycline), anti-hemorrhoidals, psychotropics, anti-diarrheals, mucolytics, decongestants (e.g., pseudoephedrine), laxatives, vitamins, and the pharmaceutically acceptable salts, complexes, stereoisomers, ethers, esters, hydrates, solvates, and mixtures thereof.

Hydrocodone Embodiments

The controlled release oral dosage forms of the present invention preferably include from about 0.5 mg to about 1250 mg hydrocodone or an equivalent amount of a pharmaceutically acceptable salt thereof. In other embodiments, the dosage forms contain from about 2 mg to about 200 mg hydrocodone or an equivalent amount of a pharmaceutically acceptable salt thereof, or from about 16 mg to about 120 mg hydrocodone or an equivalent amount of a pharmaceutically acceptable salt thereof. In certain preferred embodiments, the dosage form contains about 20 mg, about 30 mg, about 40 mg, about 60 mg, about 80 mg, about 100 mg or about 120 mg hydrocodone bitartrate.

Suitable pharmaceutically acceptable salts of hydrocodone include hydrocodone bitartrate, hydrocodone bitartrate hydrate, hydrocodone hydrochloride, hydrocodone p-toluenesulfonate, hydrocodone phosphate, hydrocodone thiosemicarbazone, hydrocodone sulfate, hydrocodone trifluoroacetate, hydrocodone hemipentahydrate, hydrocodone pentafluoropropionate, hydrocodone p-nitrophenylhydrazone, hydrocodone o-methyloxime, hydrocodone semicarbazone, hydrocodone hydrobromide, hydrocodone mucate, hydrocodone oleate, hydrocodone phosphate dibasic, hydrocodone phosphate monobasic, hydrocodone inorganic salt, hydrocodone organic salt, hydrocodone acetate trihydrate, hydrocodone bis(heptafuorobutyrate), hydrocodone bis(m-ethylcarbamate), hydrocodone bis(pentafluoropropionate), hydrocodone bis(pyridine carboxylate), hydrocodone bis (trifluoroacetate), hydrocodone chlorhydrate, and hydrocodone sulfate pentahydrate. Preferably, the hydrocodone is present as the bitartrate salt.

A hydrocodone dosage form of the present invention may further include one or more additional drugs, which may or may not act synergistically with the hydrocodone contained therein. Examples of such additional drugs include non-steroidal anti-inflammatory agents, including ibuprofen, diclofenac, naproxen, benoxaprofen, flurbipro fen, fenoprofen, flubufen, ketoprofen, indoprofen, piroprofen, carpro fen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid tolfenamic acid, diflurisal, flufenisal, piroxicam, sudoxicam, isoxicam and the pharmaceutically acceptable salts, complexes, stereoisomers, ethers, esters, hydrates, solvates, and mixtures thereof. Such non-steroidal anti-inflammatory agents also include cyclo-oxygenase inhibitors such as celecoxib, meloxicam, nabumetone, nimesulide and the pharmaceutically acceptable salts, complexes, stereoisomers, ethers, esters, hydrates, solvates, and mixtures thereof.

Other additional drugs that can be co-formulated with hydrocodone include NMDA receptor antagonists such as dextrorphan, dextromethorphan, 3-(1-naphthalennyl)-5-(phosphonomethyl)-L-phenylalanine, 3-(1-naphthalenyl)-5-(phosphonomethyl)-DL-phenylalanine, 1-(3,5-dimethylphenyl)naphthalene, 2-(3,5-dimethylphenyl) naphthalene, 2SR, 4RS-4-(((1H-Tetrazol-5-yl)methyl)oxy)piperidine-2-carboxylic acid, 2SR,4RS-4-((((1H-Tetrazol-5-yl) methypoxy)methyl)piperidine-2-carboxylic acid, E and Z 2SR-4-(0-(1H-Tetrazol-5-yl)methyl)ketoximino)piperidine-2-carboxylic acid, 2SR,4RS-4-((1H-Tetrazol-5-yl)thio)piperidine-2-carboxylic acid, 2SR,4RS-4-((1H-Tetrazol-5-yl) thio)piperidine-2-carboxylic acid, 2 SR,4RS-4-(5-mercapto-1H-Tetrazol-1-yl)piperidine-2-carboxylic acid, 2SR,4RS-4-(5-mercapto-2H-Tetrazol-2-yl)piperidine-2-carboxylic acid, 2SR,4RS-4-(5-mercapto-1H-Tetrazol-1-yl) piperidine-2-carboxylic acid, 2SR,4RS-4-(5-mercapto-2H-Tetrazol-2-yl) piperidine-2-carboxylic acid, 2SR,4RS-4-(((1H-Tetrazol-5-yl)thio)methyl)piperidine-2-carboxylic acid, 2SR,4RS-4-((5-mercapto-1H-Tetrazol-1-yl)methyl) piperidine-2-carboxylic acid, 2SR,4RS-4-((5-mercapto-2H-Tetrazol-2-yl) methyl)piperidine-2-carboxylic acid, and the pharmaceutically acceptable salts, complexes, stereoisomers, ethers, esters, hydrates, solvates, and mixtures thereof.

Other suitable drugs which may be included in the hydrocodone dosage forms of the present invention include acetaminophen and aspirin.

In preferred embodiments, the hydrocodone formulations of the present invention are suitable for once-a-day administration and provide a relatively flat plasma profile, meaning that the plasma level of the hydrocodone provides a $C_{24}/C_{max}$ ratio of about 0.55 to about 1.0 after administration. In certain embodiments, the $C_{24}/C_{max}$ ratio is about 0.55 to about 0.85, about to about 0.75 or about 0.60 to about 0.70 after administration of the dosage form.

In preferred embodiments, the hydrocodone formulations of the present invention provide a $T_{max}$ (h) of hydrocodone from about 4 to about 20 hours after administration. In certain embodiments, the $T_{max}$ is about 6 to about 12 hours, about 8 to about 10 hours, about 4 to about hours, about 8 to about 14 hours, or about 14 to about 20 hours after administration of the dosage form.

In still other embodiments, a solid controlled release dosage form of the present invention provides an AUC (ng*h/mL) after administration of about 200 to 450 or about 250 to 400 per each 20 mg hydrocodone or pharmaceutically acceptable salt thereof included in the dosage form.

In certain embodiments, a solid controlled release dosage form that contains 20 mg hydrocodone or a pharmaceutically acceptable salt thereof provides an AUC (ng*h/mL) after administration of about 200 to about 450, about 250 to about 400, about 275 to about 350, about 300 to 330 or about 280 to about 320.

In certain embodiments, a solid controlled release dosage form that contains 120 mg hydrocodone or a pharmaceutically acceptable salt thereof provides an AUC (ng*h/mL) after administration of about 1000 to about 3000, about 1500 to about 2400, about 1700 to about 2200, about 1800 to about 2100 or about 1900 to about 2100.

In other embodiments, a solid controlled release dosage form of the present invention provides a $C_{max}$ (ng/mL) after administration of about 5 to about 40, about 10 to about 30 per each 20 mg hydrocodone included in the dosage form.

In certain embodiments, a solid controlled release dosage form that contains 20 mg hydrocodone or a pharmaceutically acceptable salt thereof provides a $C_{max}$ (ng/mL) after administration of about 5 to about 40, about 10 to about 30, about 12 to about 25, about 14 to about 18 or about 12 to about 17.

In certain embodiments, a solid controlled release dosage form that contains 120 mg hydrocodone or a pharmaceutically acceptable salt thereof provides a $C_{max}$ (ng/mL) after administration of about 30 to about 120, about 60 to about 180, about 100 to about 160, about 110 to about 150 or about 100 to about 140.

In certain embodiments, a solid controlled release dosage form of the present invention provides a $T_{max}$ (h) of hydrocodone after administration of about 7 to about 22, 10 to about 20, about 12 to about 18, about 13 to about 17 or about 14 to about 16.

In other embodiments, a solid controlled release dosage form of the present invention provides a $T_{1/2}$ (h) of hydrocodone after administration of about 5 to about 10, about 6 to about 9, about 7 or about 8.

In other embodiments, a solid controlled release dosage form of the present invention provides a $T_{lag}$ (h) of hydrocodone after administration of about 0.01 to about 0.2, about 0.1 to about 0.18, about 0.3 to about 0.17 or about 0.06 t about 0.15.

In other embodiments, a solid controlled release dosage form of the present invention provides a $C_{24}/C_{max}$ ratio of hydrocodone of about 0.2 to about 0.8, about 0.3 to about 0.7 or about 0.4 to about 0.6.

In certain embodiments, any one or all of the above mean in vivo parameters are achieved after administration in the fasted state.

In certain embodiments, the mean AUC (ng*h/mL) of hydrocodone after administration in the fed state is less than 20% higher, less than 16% higher or less than 12% higher than the AUC (ng*h/mL) of hydrocodone after administration in the fasted state.

In certain embodiments, the mean $C_{max}$ (ng/mL) of hydrocodone after administration in the fed state is less than 80% higher, less than 70% higher or less than 60% higher than the $C_{max}$ of hydrocodone after administration in the fasted state.

In certain embodiments, the mean $T_{max}$ (h) of hydrocodone after administration in the fed state is within 25%, within 20% or within 15% of the $T_{max}$ of hydrocodone after administration in the fasted state.

In certain embodiments, the mean $T_{1/2}$ (h) of hydrocodone after administration in the fed state is within 8%, within 5% or within 2% of the $T_{1/2}$ after administration in the fasted state.

In certain embodiments, the mean $T_{lag}$ of hydrocodone after administration in the fed state is less than 150% higher, less than 125% higher or less than 100% higher than the $T_{1/2}$ after administration in the fasted state.

In certain embodiments, any one or all of the above in vivo parameters are achieved after a first administration of the dosage form to a human subject, patient, or healthy subject (individual data) or a population of human subjects, patients or healthy subjects (mean data).

In certain alternative embodiments, any one or all of the above in vivo parameters are achieved after steady state administration of the dosage form to a human subject, patient or healthy subject or a population of human subjects, patients or healthy subjects.

Cured Formulations

In certain embodiments, a process of the present invention further comprises the step of curing the final dosage form.

For embodiments comprising polyethylene oxide in a controlled release formulation, the curing step may comprise at least partially melting the polyethylene oxide in the formulation. In certain embodiments, at least about 20% or at least about 30% of the polyethylene oxide in the formulation melts. Preferably, at least about 40%, or at least about 50%, or at least about 60%, or at least about 75%, or at least about 90% of the polyethylene oxide in the formulation melts during the curing step. In a preferred embodiment, about 100% of the polyethylene oxide melts.

In other embodiments, the curing step comprises subjecting the formulation to an elevated temperature for a certain period of time. In such embodiments, the curing temperature is at least as high as the softening temperature of the polyethylene oxide. According to certain embodiments, the curing temperature is at least about 60° C., at least about 62° C., ranges from about 62° C. to about 90° C., from about 62° C. to about 85° C., from about 62° C. to about 80° C., from about 65° C. to about 90° C., from about 65° C. to about 85° C., or from about 65° C. to about 80° C. The curing temperature preferably ranges from about 68° C. to about 90° C., from about 68° C. to about 85° C., from about 68° C. to about 80° C., from about 70° C. to about 90° C., from about 70° C. to about 85° C., from about 70° C. to about 80° C., from about 72° C. to about 90° C., from about 72° C. to about 85° C. or from about 72° C. to about 80° C. The curing temperature may be at least about 60° C., at least about 62° C., less than about 90° C. or less than about 80° C. Preferably, it is in the range of from about 62° C. to about 72° C. or from about 68° C. to about 72° C. Preferably, the curing temperature is at least as high as the lower limit of the softening temperature range of the polyethylene oxide, or at least about 62° C., or at least about 68° C. More preferably, the curing temperature is within the softening temperature range of the polyethylene oxide, or at least about 70° C. In further embodiments, the curing temperature is at least as high as the upper limit of the softening temperature range of the polyethylene oxide, or at least about 72° C. In further embodiments, the curing temperature is higher than the upper limit of the softening temperature range of the polyethylene oxide, or at least about 75° C., or at least about 80° C.

In those embodiments where the curing step involves subjecting the formulation to an elevated temperature for a certain period of time, this period of time is hereinafter referred to as the curing time. For the measurement of the curing time, a starting point and an end point of the curing step are defined. For the purposes of the present invention, the starting point of the curing step is defined to be the point in time when the curing temperature is reached.

In certain embodiments, the temperature profile during the curing step shows a plateau-like form between the starting point and the end point of the curing. In such embodiments, the end point of the curing step is defined to be the point in time when the heating is stopped or at least reduced, e.g. by terminating or reducing the heating and/or by starting a subsequent cooling step, and the temperature subsequently drops below the curing temperature by more than about and/or below the lower limit of the softening temperature range of polyethylene oxide, for example, below about 62° C. When the curing temperature is reached and the curing step is thus started, deviations from the curing temperature in the course of the curing step can occur. Such deviations are tolerated as long as they do not exceed a value of about ±10° C., preferably about ±6° C., and more preferably about ±3° C. For example, if a curing temperature of at least about is to be maintained, the measured temperature may temporarily increase to a value of about 85° C., about 81° C., or about 78° C., and the measured temperature may also temporarily drop down to a value of about 65° C., about 69° C. or about 72° C. In the cases of a larger decrease of the temperature and/or in the case that the temperature drops below the lower limit of the softening temperature range of polyethylene oxide, for example below about 62° C., the curing step is discontinued, i.e. an end point is reached. Curing can be restarted by again reaching the curing temperature.

In other embodiments, the temperature profile during the curing step shows a parabolic or triangular form between the starting point and the end point of the curing. This means that after the starting point, i.e., the point in time when the curing temperature is reached, the temperature further increases to reach a maximum, and then decreases. In such embodiments, the end point of the curing step is defined to be the point in time when the temperature drops below the curing temperature.

Depending on the apparatus used for the curing (i.e., curing device), different temperatures within the curing device can be measured to characterize the curing temperature.

In certain embodiments, the curing step may take place in an oven. In such embodiments, the temperature inside the oven is measured. Based thereon, when the curing step takes place in an oven, the curing temperature is defined to be the target inside temperature of the oven and the starting point of the curing step is defined to be the point in time when the inside temperature of the oven reaches the curing temperature. The end point of the curing step is defined to be (1) the point in time when the heating is stopped or at least reduced and the temperature inside the oven subsequently drops below the curing temperature by more than about 10° C. and/or below the lower limit of the softening temperature range of high molecular weight polyethylene oxide, for example below about 62° C., in a plateau-like temperature profile or (2) the point in time when the temperature inside the oven drops below the curing temperature in a parabolic or triangular temperature profile. Preferably, the curing step starts when the temperature inside the oven reaches a curing temperature of at least about 62° C., at least about 68° C., at least about 70° C., at least about 72° C. or at least about 75° C. In preferred embodiments, the temperature profile during the curing step shows a plateau-like form, wherein the curing temperature, i.e. the inside temperature of the oven, is at least about 68° C., about 70° C., about 72° C., about 73° C., or lies within a range of from about 70° C. to about 75° C., and the curing time is preferably in the range of from about 30 minutes to about 20 hours, from about 30 minutes to about 15 hours, from about 30 minutes to about 4 hours, or from about 30 minutes to about 2 hours. In certain embodiments, the curing time is in the range of from about 30 minutes to about 90 minutes.

In certain other embodiments, the curing takes place in curing devices that are heated by an air flow and comprise a heated air supply (inlet) and an exhaust, e.g., a coating pan or fluidized bed. Such curing devices will hereinafter be called convection curing devices. In such curing devices, it is possible to measure the temperature of the inlet air, i.e., the temperature of the heated air entering the convection curing device and/or the temperature of the exhaust air, i.e., the temperature of the air leaving the convection curing device. It is also possible to determine or at least estimate the temperature of the formulations inside the convection curing device during the curing step, e.g., by using infrared temperature measurement instruments (such as an IR gun) or by measuring the temperature using a temperature probe that was placed inside the curing device near the formulations. Based thereon, when the curing step takes place in a convection curing device, the curing temperature can be defined and the curing time can be measured as follows.

In one embodiment (method 1), the curing temperature is defined to be the target inlet air temperature and the starting point of the curing step is defined to be the point in time when the inlet air temperature reaches the curing temperature. The end point of the curing step is defined to be (1) the point in time when the heating is stopped or at least reduced and the inlet air temperature subsequently drops below the curing temperature by more than about 10° C. and/or below the lower limit of the softening temperature range of high molecular weight polyethylene oxide, for example below about 62° C., in a plateau-like temperature profile, or (2) the point in time when the inlet air temperature drops below the curing temperature in a parabolic or triangular temperature profile. Preferably, the curing step starts according to method 1, when the inlet air temperature reaches a curing temperature of at least about 62° C., at least about 68° C., at least about 70° C., at least about 72° C. or at least about 75° C. In a preferred embodiment, the temperature profile during the curing step shows a plateau-like form, wherein the curing temperature, i.e. the target inlet air temperature, is preferably at least about 72° C., for example, about 75° C., and the curing time which is measured according to method 1 is preferably in the range of from about 15 minutes to about 2 hours, for example, about 30 minutes or about 1 hour.

In another embodiment (method 2), the curing temperature is defined to be the target exhaust air temperature, and the starting point of the curing step is defined to be the point in time when the exhaust air temperature reaches the curing temperature. The end point of the curing step is defined to be (1) the point in time when the heating is stopped or at least reduced and the exhaust air temperature subsequently drops below the curing temperature by more than about 10° C. and/or below the lower limit of the softening temperature range of high molecular weight polyethylene oxide, for example below about 62° C., in a plateau-like temperature profile, or (2) the point in time when the exhaust air temperature drops below the curing temperature in a parabolic or triangular temperature profile. Preferably, the curing step starts according to method 2, when the exhaust air temperature reaches a curing temperature of at least about 62° C., at least about 68° C., at least about 70° C., at least about 72° C. or at least about 75° C. In preferred embodiments, the temperature profile during the curing step shows a plateau-like form, wherein the curing temperature, i.e. the target exhaust air temperature, is preferably at least about 68° C., at least about 70° C. or at least about 72° C., for example the target exhaust air temperature is about 68° C., about 70° C., about 72° C., about 75° C. or about 78° C., and the curing time which is measured according to method 2 is preferably in the range of from about 1 minute to about 2 hours or from about 5 minutes to about 90 minutes, for example, the curing time is about 5 minutes, about 10 minutes, about 15 minutes, about 30 minutes, about 60 minutes, about 70 minutes, about 75 minutes or about 90 minutes. In a more preferred embodiment, the curing time which is measured according to method 2 is in the range of from about 15 minutes to about 1 hour.

In a further embodiment (method 3), the curing temperature is defined to be the target temperature of the formulations and the starting point of the curing step is defined to be the point in time when the temperature of the formulations, which can be measured for example by an IR gun, reaches the curing temperature. The end point of the curing step is defined to be (1) the point in time when the heating is stopped or at least reduced and the temperature of the formulations subsequently drops below the curing temperature by more than about 10° C. and/or below the lower limit of the softening temperature range of high molecular weight polyethylene oxide, for example below about 62° C., in a plateau-like temperature profile or (2) the point in time when the temperature of the formulations drops below the curing temperature in a parabolic or triangular temperature profile. Preferably, the curing step starts according to method 3, when the temperature of the formulations reaches a curing temperature of at least about 62° C., at least about 68° C., at least about 70° C., at least about 72° C. or at least about 75° C.

In still another embodiment (method 4), the curing temperature is defined to be the target temperature measured using a temperature probe, such as a wire thermocouple, that is placed inside the curing device near the formulations, and the starting point of the curing step is defined to be the point in time when the temperature measured using the temperature probe reaches the curing temperature. The end point of the curing step is defined to be (1) the point in time when the heating is stopped or at least reduced and the temperature measured using the temperature probe subsequently drops below the curing temperature by more than about 10° C. and/or below the lower limit of the softening temperature range of polyethylene oxide, for example below about 62° C., in a plateau-like temperature profile, or (2) the point in time when the temperature measured using the temperature probe drops below the curing temperature in a parabolic or triangular temperature profile. Preferably, the curing step starts when the temperature measured using a temperature probe registers a temperature in the curing device of at least about 62° C., at least about 68° C., at least about 70° C., at least about 72° C. or at least about 75° C. In a preferred embodiment, the temperature profile during the curing step shows a plateau-like form, wherein the curing temperature is at least about 68° C., for example, about and the curing time which is measured according to method 4 is preferably in the range of from about 15 minutes to about 2 hours or about 60 minutes or about 90 minutes.

If curing takes place in a convection curing device, the curing time can be measured by any of the methods described above.

In certain embodiments, the curing temperature is defined as a target temperature range, for example, the curing temperature is defined as a target inlet air temperature range or a target exhaust air temperature range. In such embodiments, the starting point of the curing step is defined to be the point in time when the lower limit of the target temperature range is reached, and the end point of the curing step is defined to be the point in time when the heating is stopped or at least reduced, and the temperature subsequently drops below the lower limit of the target temperature range by more than about 10° C. and/or below the lower limit of the softening temperature range of polyethylene oxide, for example, below about 62° C.

The curing time, i.e., the time period the formulation is subjected to the curing temperature, which can, for example, be measured according to the methods described above, is at least about 1 minute or at least about 5 minutes. The curing time may vary from about 1 minute to about 24 hours, from about 5 minutes to about 20 hours, from about 10 minutes to about 15 hours, from about 15 minutes to about 10 hours, or from about 30 minutes to about 5 hours depending on the specific formulation and the curing temperature. According to certain embodiments, the curing time varies from about 15 minutes to about 30 minutes. According to further embodiments, wherein the curing temperature is at least about 60° C., at least about 62° C., at least about 68° C., at least about 70° C., at least about 72° C. or at least about 75° C., or varies from about 62° C. to about 85° C. or from about 65° C. to about 85° C., then the curing time is preferably at least about 15 minutes, at least about 30 minutes, at least about 60 minutes, at least about 75 minutes, at least about 90 minutes or at least about 120 minutes. In preferred embodiments, wherein the curing temperature is, for example, at least about 62° C., at least about 68° C., at least about 70° C., at least about 72° C. or at least about 75° C., or ranges from about 62° C. to about 80° C., from about 65° C. to about 80° C., from about 68° C. to about 80° C., from about 70° C. to about 80° C. or from about 72° C. to about 80° C., then the curing time is preferably at least about 1 minute, at least about 5 minutes, at least about 10 minutes, at least about 15 minutes or at least about 30 minutes. In certain such embodiments, the curing time can be chosen to be as short as possible while still achieving the desired result (e.g., increased tamper resistance). For example, the curing time preferably does not exceed about 5 hours, does not exceed about 3 hours or does not exceed about 2 hours. Preferably, the curing time is in the range of from about 1 minute to about 5 hours, from about 5 minutes to about 3 hours, from about 15 minutes to about 2 hours, or from about 15 minutes to about 1 hour. Any combination of the curing temperatures and the curing times as disclosed herein lies within the scope of the present invention.

In certain embodiments, the composition is only subjected to the curing temperature until the polyethylene oxide present in the formulation has reached its softening temperature and/or at least partially melts. In certain such embodiments, the curing time may be less than about 5 minutes, for example the curing time may vary from greater than 0 minutes to about 3 hours, from about 1 minute to about 2 hours or from about 2 minutes to about 1 hour. Instant curing is possible by choosing a curing device which allows for an instant heating of the polyethylene oxide in the formulation to at least its softening temperature, so that the high molecular weight polyethylene oxide at least partially melts. Such curing devices are, for example, microwave ovens, ultrasound devices, light irradiation apparatus such as UV-irradiation apparatus, ultra-high frequency (UHF) fields or any other apparatus known to the person skilled in the art.

The size of the formulation may determine the required curing time and curing temperature to achieve the desired tamper resistance.

In certain embodiments, the curing step leads to a decrease in the density of the formulation, such that the density of the cured formulation is lower than the density of the formulation prior to the curing step. Preferably, the density of the cured formulation in comparison to the density of the uncured formulation decreases by at least about 0.5%. More preferably, the density of the cured formulation in comparison to the density of the uncured formulation decreases by at least about 0.7%, at least about 0.8%, at least about 1.0%, at least about 2.0% or at least about 2.5%.

In certain embodiments, the solid controlled release dosage form is cured at a temperature of at least the softening point of the polyethylene oxide for at least 1 minute, at least 5 minutes or at least 15 minutes.

In other embodiments, the solid controlled release dosage form is cured at a temperature of at least the softening point of the polyethylene oxide from about 1 minute to about 48 hours, from about 5 minutes to about 24 hours, from about 15 minutes to about 1 hour or about 30 minutes.

The solid controlled release dosage form can be cured, e.g., at a temperature of at least about 60° C., at least about 65° C., at least about 70° C., at least about 75° C. or at a temperature of about 72° C.

In alternative embodiments, the solid controlled release dosage form can be cured at a temperature from about 60° C. to about 90° C., from about 62° C. to about 72° C., from about 65° C. to about 85° C., from about 70° C. to about 80° C., from about 75° C. to about 80° C. or from about 70° C. to about 75° C.

Flattening Procedures

In certain embodiments, dosage forms of the present invention may be flattened without substantially compromising the release of the active or the integrity of the dosage form. Flatness is described in terms of the thickness of the smallest diameter of the flattened shape compared to the thickness of the smallest diameter of the non-flattened shape. This comparison is expressed in % thickness, based on either (i) the thickness of the smallest diameter of the non-flattened shape when the initial shape is non-spherical or (ii) the thickness of the diameter when the initial shape is spherical. The thickness may be measured using a thickness gauge (e.g., a digital thickness gauge or digital caliper). The flattening force may be applied by any possible method. For purposes of testing the dosage forms of the present invention, a carver style bench press may be used (unless otherwise specified) so as to achieve the target flatness or reduced thickness. According to certain embodiments of the invention, the flattening does not result in breaking of the dosage form into separate pieces; however, edge splits and cracks may occur.

In certain embodiments of the invention, a hammer can be used for flattening a dosage form. In such a process, hammer strikes can be manually applied from a direction substantially normal to the thickest dimension of the dosage form. The flatness is then described in the same manner as disclosed above.

In other embodiments, flattening can be measured relative to breaking strength or hardness tests, as described in Remington's Pharmaceutical Sciences, 18th edition, 1990, Chapter 89 "Oral Solid Dosage Forms", pages 1633-1665, using the Schleuniger Apparatus. In such an embodiment, the dosage form is pressed between a pair of flat plates arranged in parallel such that the force is applied substantially normal to the thickest dimension of the dosage form, thereby flattening the dosage form. The flattening of the dosage form may be described in terms of % flattening, based on the thickness of the dimension being flattened before conducting the breaking strength test. The breaking strength (or hardness) is defined as the force at which the tested dosage form breaks. Dosage forms that do not break, but which are deformed due to a force applied are considered to be break-resistant at that particular force.

A further test to quantify the strength of dosage forms is the indentation test using a Texture Analyzer, such as the TA-XT2 Texture Analyzer (Texture Technologies Corp., 18 Fairview Road, Scarsdale, N.Y. 10583). In this method, a dosage form is placed on top of a stainless steel stand with a slightly concave surface and penetrated by the descending probe of the Texture Analyzer, such as a TA-8A ⅛ inch diameter stainless steel ball probe. Before starting the measurement, the dosage form is aligned directly under the probe, such that the descending probe will penetrate the tablet pivotally, i.e., in the center of the dosage form, and such that the force of the descending probe is applied substantially perpendicular to the diameter and substantially in line with the thickness of the dosage form. First, the probe of the Texture Analyzer starts to move towards the dosage form sample at the pre-test speed. When the probe contacts the dosage form surface and the trigger force set is reached, the probe continues its movement with the test speed and penetrates the dosage form. For each penetration depth or distance of the probe, the corresponding force is measured. When the probe has reached the desired maximum penetration depth, it changes direction and moves back at the post-test speed, while further measurements are taken. The cracking force is defined to be the force of the first local maximum that is reached in the corresponding force/distance diagram and is calculated using, for example, the Texture Analyzer software "Texture Expert Exceed, Version 2.64 English".

The term "resistant to crushing" is defined for the purposes of certain embodiments of the present invention as referring to dosage forms that can at least be flattened with a bench press as described above without breaking to no more than about 60% thickness, preferably no more than about 50% thickness, more preferred no more than about 40% thickness, even more preferred no more than about 30% thickness and most preferred no more than about 20% thickness, 10% thickness or 5% thickness.

In certain embodiments, the amount of active agent (e.g., opioid analgesic) released at hour from a flattened dosage form deviates no more than about 10% points, 15% points or 20% points from the amount released at 0.5 hour from a non-flattened dosage form as measured by an in-vitro dissolution in a USP Apparatus 1 (basket) at 100 rpm in 900 ml simulated gastric fluid without enzymes (SGF) at 37° C.

In alternative embodiments, the solid controlled release dosage form can be flattened without breaking, wherein the thickness of the dosage form after flattening corresponds to no more than about 60% of the thickness of the dosage form before flattening, no more than about 50% of the thickness of the dosage form before flattening, no more than about 40% of the thickness of the dosage form before flattening, no more than about 30% of the thickness of the dosage form before flattening or no more than about 20% of the thickness of the dosage form before flattening.

The following examples are set forth to assist in understanding the invention and should not be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the invention incorporated herein.

EXAMPLES

The present invention will now be more fully described with reference to the accompanying examples. It should be understood, however, that the following description is illustrative only and should not be taken in any way as a restriction of the invention.

Example 1

A 400 mg tablet (Tablet A) including 20 mg of hydrocodone bitartrate was prepared using high molecular weight polyethylene oxide (PEO 303—MW 7,000,000), as set forth in Table 1 below.

TABLE 1

(Tablet A)

| | Hydrocodone (mg) | Total wt | % of Hydrocodone | Tooling Size (mm) |
|---|---|---|---|---|
| Core | 16 | 200 | 8 | 7.94 |
| Shell | 4 | 200 | 2 | 10.32 |
| Total | 20 | 400 | 10 | |

To prepare the core, a single station Manesty Type F 3 tablet press was equipped with 7.94 mm, round, standard concave plain tooling. A powdered aliquot of the core blend, as set forth above in Table 1, was weighed out to target weight of 200 mg, charged into the die, and compressed to form the core of Tablet A.

To prepare the shell, the single station Manesty Type F 3 tablet press was equipped with mm, round, standard concave plain tooling. 100 mg of the shell blend, as set forth in Table 1, was placed in the die. The tablet core as prepared above was manually centered in the die (on top of the powder bed), and an additional 100 mg of the shell blend was placed on top of the tablet in the die. The materials were then manually compressed by turning the compression wheel to form compression coated Tablet A.

Several compression coated Tablet A tablets prepared as above were placed onto a tray, which was placed in a Hotpack model 435304 oven targeting 72° C. for 30 minutes to cure.

Dissolution of cured Tablet A tablets was then tested in a USP Apparatus 1 (basket) at 100 rpm in 900 ml simulated gastric fluid without enzymes (SGF) at 37° C. Results are shown against the results of the formulations of Examples 2-4 in FIG. 1.

Example 2

A 500 mg tablet (Tablet B) including 20 mg of hydrocodone bitartrate was prepared using high molecular weight polyethylene oxide (PEO 303—MW 7,000,000), as set forth in Table 2 below.

TABLE 2

(Tablet B)

|  | Hydrocodone (mg) | Total wt | % of Hydrocodone | Tooling Size (mm) |
| --- | --- | --- | --- | --- |
| Core | 16 | 300 | 5.3 | 8.73 |
| Shell | 4 | 200 | 2 | 11.11 |
| Total | 20 | 500 | 4 | |

To prepare the core, a single station Manesty Type F 3 tablet press was equipped with 8.73 mm, round, standard concave plain tooling. A powdered aliquot of the core blend, as set forth above in Table 2, was weighed out to target weight of 300 mg, charged into the die and compressed to form the core of Tablet B.

To prepare the shell, the single station Manesty Type F 3 tablet press was equipped with 11.11 mm, round, standard concave plain tooling. The first portion of the 200 mg shell blend, as set forth in Table 2, was placed in the die. The tablet core as prepared above was manually centered in the die (on top of the powder bed), and the remaining portion of the 200 mg shell blend was placed on top of the tablet in the die. The materials were then manually compressed by turning the compression wheel to form compression coated Tablet B.

Several compression coated Tablet B tablets prepared as above were placed onto a tray, which was placed in a Hotpack model 435304 oven targeting 72° C. for 30 minutes to cure.

Dissolution of cured Tablet B tablets was then tested in a USP Apparatus 1 (basket) at 100 rpm in 900 ml simulated gastric fluid without enzymes (SGF) at 37° C. Results are shown against the results of the formulations of Examples 1 and 3-4 in FIG. 1.

Example 3

A 500 mg tablet (Tablet C) including 20 mg of hydrocodone bitartrate was prepared using high molecular weight polyethylene oxide (PEO 303—MW 7,000,000), as set forth in Table 3 below.

TABLE 3

(Tablet C)

|  | Hydrocodone (mg) | Total wt | % of Hydrocodone | Tooling Size (mm) |
| --- | --- | --- | --- | --- |
| Core | 16 | 300 | 5.3 | 9.53 |
| Shell | 4 | 200 | 2 | 11.11 |
| Total | 20 | 500 | 4 | |

To prepare the core, a single station Manesty Type F 3 tablet press was equipped with 9.53 mm, round, standard concave plain tooling. A powdered aliquot of the core blend, as set forth above in Table 3, was weighed out to target weight of 300 mg, charged into the die and compressed to form the core of Tablet C.

To prepare the shell, the single station Manesty Type F 3 tablet press was equipped with 11.11 mm, round, standard concave plain tooling. A first portion of the 200 mg shell blend, as set forth in Table 3, was placed in the die. The tablet core as prepared above was manually centered in the die (on top of the powder bed), and the remaining portion of the 200 mg shell blend was placed on top of the tablet in the die. The materials were then manually compressed by turning the compression wheel to form compression coated Tablet C.

Several compression coated Tablet C tablets prepared as above were placed onto a tray, which was placed in a Hotpack model 435304 oven targeting 72° C. for 30 minutes to cure.

Dissolution of cured Tablet C tablets was then tested in a USP Apparatus 1 (basket) at 100 rpm in 900 ml simulated gastric fluid without enzymes (SGF) at 37° C. Results are shown against the results of the formulations of Examples 1-2 and 4 in FIG. 1.

Example 4

A 475 mg tablet (Tablet D) including 20 mg of hydrocodone bitartrate was prepared using high molecular weight polyethylene oxide (PEO 303—MW 7,000,000), as set forth in Table 4 below.

TABLE 4

(Tablet D)

|  | Hydrocodone (mg) | Total wt | % of Hydrocodone | Tooling Size (mm) |
| --- | --- | --- | --- | --- |
| Core | 14 | 175 | 8 | 7.94 |
| Shell | 6 | 300 | 2 | 11.11 |
| Total | 20 | 475 | 4.2 | |

To prepare the core, a single station Manesty Type F 3 tablet press was equipped with 7.94 mm, round, standard concave plain tooling. A powdered aliquot of the core blend, as set forth in Table 4, was weighed out to target weight of 175 mg, charged into the die and compressed to form the core of Tablet D.

To prepare the shell, the single station Manesty Type F 3 tablet press was equipped with 11.11 mm, round, standard concave plain tooling. A first portion of the 300 mg shell blend, as set forth in Table 4, was placed in the die. The tablet core as prepared above was manually centered in the die (on top of the powder bed), and the remaining portion of the 300 mg shell blend was placed on top of the tablet in the die. The materials were then manually compressed by turning the compression wheel to form compression coated Tablet D.

Several compression coated Tablet D tablets prepared as above were then placed onto a tray, which was placed in a Hotpack model 435304 oven targeting 72° C. for 30 minutes to cure.

Dissolution of cured Tablet D tablets was then tested in a USP Apparatus 1 (basket) at 100 rpm in 900 ml simulated gastric fluid without enzymes (SGF) at 37° C. Results are shown against the results of the formulations of Examples 1-3 in FIG. 1.

Example 5

A 500 mg tablet (Tablet E) including 120 mg of hydrocodone was prepared using low molecular weight polyethylene oxide (PEO 205—MW 600,000) for the core and using high molecular weight polyethylene oxide (PEO 303—MW 7,000,000) for the shell, as set forth in Table 5 below.

TABLE 5

(Tablet E)

|  | Hydrocodone (mg) | Total wt | % of Hydrocodone | Tooling Size (mm) |
|---|---|---|---|---|
| Core | 96 | 300 | 32 | 8.73 |
| Shell | 24 | 200 | 12 | 11.11 |
| Total | 120 | 500 | 24 | |

To prepare the core, a single station Manesty Type F 3 tablet press was equipped with 8.73 mm, round, standard concave plain tooling. A powdered aliquot of the core blend, as set forth in Table 5, was weighed out to target weight of 300 mg, charged into the die and compressed to form the core of Tablet E.

To prepare the shell, the single station Manesty Type F 3 tablet press was equipped with 11.11 mm, round, standard concave plain tooling. A first portion of the 200 mg shell blend, as set forth in Table 5, was placed in the die. The tablet core as prepared above was manually centered in the die (on top of the powder bed), and the remaining portion of the 200 mg shell blend was placed on top of the tablet in the die. The materials were manually compressed by turning the compression wheel to form compression coated Tablet E.

Several compression coated Tablet E tablets prepared as above were then placed onto a tray, which was placed in a Hotpack model 435304 oven targeting 72° C. for 30 minutes to cure.

Figure 2:
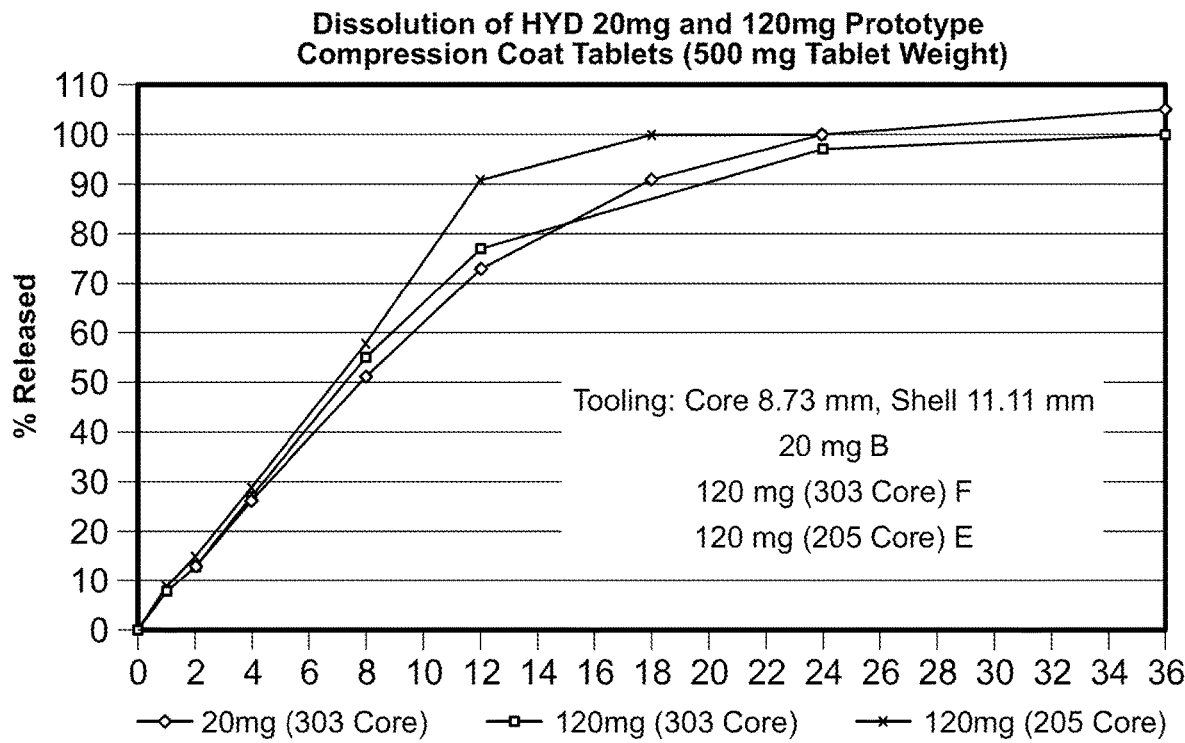
FIG. 2 is a graph that depicts the dissolution of the compositions of Examples 5 and 6.

Dissolution of cured Tablet E tablets was then tested in a USP Apparatus 1 (basket) at 100 rpm in 900 ml simulated gastric fluid without enzymes (SGF) at 37° C. Results are shown against the results of the formulations of Examples 5 and 6 in FIG. 2.

Example 6

A 500 mg tablet (Tablet F) including 120 mg of hydrocodone was prepared using high molecular weight polyethylene oxide (PEO 303—MW 7,000,000), as set forth in Table 6 below.

TABLE 6

(Tablet F)

|  | Hydrocodone (mg) | Total wt | % of Hydrocodone | Tooling Size (mm) |
|---|---|---|---|---|
| Core | 96 | 300 | 32 | 8.73 |
| Shell | 24 | 200 | 12 | 11.11 |
| Total | 120 | 500 | 24 | |

To prepare the core, a single station Manesty Type F 3 tablet press was equipped with 8.73 mm, round, standard concave plain tooling. A powdered aliquot of the core blend, as set forth in Table 6, was weighed out to target weight of 300 mg, charged into the die and compressed to form the core of Tablet F.

To prepare the shell, the single station Manesty Type F 3 tablet press was equipped with 11.11 mm, round, standard concave plain tooling. A first portion of the 200 mg shell blend, as set forth in Table 6, was placed in the die. The tablet core as prepared above was manually centered in the die (on top of the powder bed), and the remaining portion of the 200 mg shell blend was placed on top of the tablet in the die. The materials were manually compressed by turning the compression wheel to form compression coated Tablet F.

Several compression coated Tablet F tablets prepared as above were then placed onto a tray, which was placed in a Hotpack model 435304 oven targeting 72° C. for 30 minutes to cure.

Dissolution of Tablet F tablets was then tested in a USP Apparatus 1 (basket) at 100 rpm in 900 ml simulated gastric fluid without enzymes (SGF) at 37° C. Results are shown against the results of the formulations of Examples 5 and 6 in FIG. 2.

Examples 7-12

Six different compression coated tablets (designated as Tablets G-L) containing a total of either 20 mg of hydrocodone bitartrate (Tablets G, H and I) or 120 mg of hydrocodone bitartrate (Tablets J, K and L) were prepared according to Table 7 (20 mg) or Table 8 (120 mg) below.

TABLE 7

(Tablets G, H, I)

| 20 mg Component | Formulation G mg/tablet | Formulation H mg/tablet | Formulation I mg/tablet |
|---|---|---|---|
| Core | | | |
| Hydrocodone Bitartate | 16 | 16 | 16 |
| Microcrystalline Cellulose, Avicel PH 101 | 1.09 | 1.09 | 1.09 |
| Hydroxypropyl Cellulose, Klucel EXF | 1.09 | 1.09 | 1.09 |
| PEO (Mw = 600,000) POLYOX WSR 205 | 280.32 | 280.32 | 280.32 |
| Magnesium Stearate | 1.5 | 1.5 | 1.5 |
| Subtotal | 300 | 300 | 300 |
| Dry Coat | | | |
| Hydrocodone Bitartate | 4 | 4 | 4 |
| Microcrystalline Cellulose, Avicel PH 101 | 0.27 | 0.27 | 0.27 |
| Hydroxypropyl Cellulose, Klucel EXF | 0.27 | 0.27 | 0.27 |
| PEO (Mw = 7,000,000) POLYOX WSR 303 FP | 393.26 | 293.81 | 194.36 |

TABLE 7-continued (Tablets G, H, I)

| 20 mg Component | Formulation G mg/tablet | Formulation H mg/tablet | Formulation I mg/tablet |
|---|---|---|---|
| Magnesium Stearate | 2 | 1.5 | 1 |
| D&C Yellow No. 10 Aluminum Lake | 0.2 | 0.15 | 0.1 |
| Subtotal Cosmetic Coat | 400 | 300 | 200 |
| Opadry White Y-5-18024-A | 28 | 24 | 20 |
| Total | 728 | 624 | 520 |

TABLE 8

(Tablets J, K, L)

| 120 mg Component | Formulation J mg/tablet | Formulation K mg/tablet | Formulation L mg/tablet |
|---|---|---|---|
| Core | | | |
| Hydrocodone Bitartrate | 96 | 96 | 96 |
| Microcrystalline Cellulose, Avicel PH 101 | 6.54 | 6.54 | 6.54 |
| Hydroxypropyl Cellulose, Klucel EXF | 6.54 | 6.54 | 6.54 |
| PEO (Mw = 600,000) POLYOX WSR 205 | 189.42 | 189.42 | 189.42 |
| Magnesium Stearate | 1.5 | 1.5 | 1.5 |
| Subtotal | 300 | 300 | 300 |
| Dry Coat | | | |
| Hydrocodone Bitartrate | 24 | 24 | 24 |
| Microcrystalline Cellulose, Avicel PH 101 | 1.64 | 1.64 | 1.64 |
| Hydroxypropyl Cellulose, Klucel EXF | 1.64 | 1.64 | 1.64 |
| PEO (Mw = 7,000,000) POLYOX WSR 303 FP | 370.52 | 271.07 | 171.62 |
| Magnesium Stearate | 2 | 1.5 | 1 |
| D&C Red No. 30 Aluminum Lake | 0.2 | 0.15 | 0.1 |
| Subtotal Cosmetic Coat | 400 | 300 | 200 |
| Opadry Pink Y-S-1-14518A | 28 | 24 | 20 |
| Total | 728 | 624 | 520 |

A high-shear granulator (Collette 75 L) was charged with the hydrocodone bitartrate, the microcrystalline cellulose and the hydroxypropylcellulose. Water was added to the mixture (e.g., 8-15%) with the propeller and chopper on. The wet granulation was passed through the coarse screen of a Quadro Comil milling device. The screened wet granulation was dried in a Vector VFC-3 fluid bed dryer. The dried granulation was passed through the fine screen of the Quadro Comil milling device.

A 16 Q "V" blender was charged with the PEO POLYOX WSR 205 and the milled granulation, and blended for 5 minutes. Screened magnesium stearate was added to the mixture and blended for 1 minute to prepare the core blend.

A 16 Q "V" blender was charged with the PEO POLYOX WSR 303, the D&C Red No. 30 aluminum lake, and the milled granulation, and blended for 5 minutes. Screened magnesium stearate was added to the mixture and blended for 1 minute to prepare the dry coat blend.

The core blend and dry coat blend were compressed into dry coated tablets on a DryCota Press. The core blend was loaded into the side one hopper and the core weight was adjusted to target 300 mg. Then the dry coat blend was loaded into the side two hopper and the total tablet weight was adjusted to target. After weight adjustment, the compression run was started and the press was run at, e.g., 6 rpm.

Approximately 10 kg of the compression coated tablets were weighed out and spray-coated with the Opadry coating suspension to a target weight gain of about 1.0% (by wt.) in a perforated 24 inch Compu-Lab pan coater. The spray-coating was carried out as follows. The tablet bed was warmed by setting the inlet air temperature to 55° C. Once the exhaust temperature reached 39° C., the film coating began at a pan speed of 12 rpm and a spray rate of approximately 44 mL/min. Film coating was continued until the target 1% weight gain was achieved (this was a partial coating prior to the curing in step x, as the final coating of 4% weight gain in step xii would become sticky during curing).

The partially coated tablets were cured in the perforated pan coater. The inlet temperature was set to 85° C. at a pan speed of approximately 10 rpm. The tablets were cured at an exhaust temperature of 72° C. for approximately 30 minutes.

After curing, the tablets were cooled in the rotating pan by setting the inlet temperature to 22° C. Cooling was continued until the exhaust temperature was less than 28° C.

The cured tablets were then spray-coated with additional coating suspension to attain a target final weight gain of 4.0% (by wt., inclusive of the previous 1% coating) in the perforated pan coater at a pan speed of 12 rpm and spray rate of approximately 44 mL/min.

The film coated tablets were transferred into a tared polyethylene lined drum.

Figure 3:
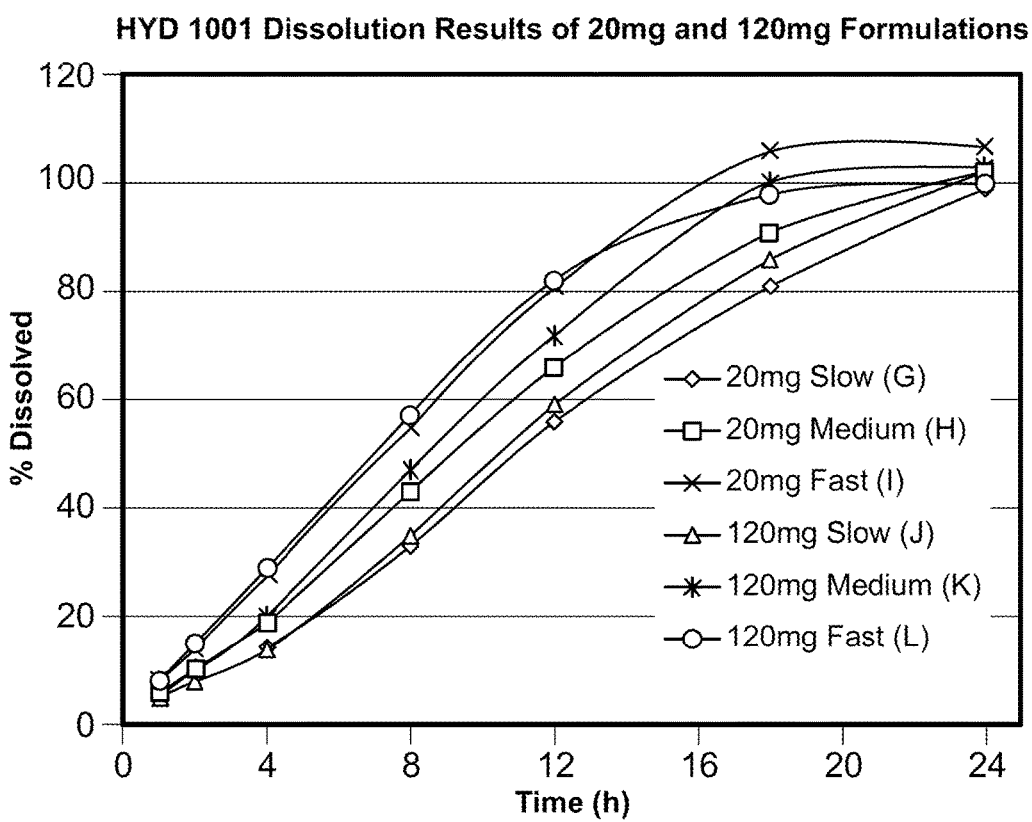
FIG. 3 is a graph that depicts the dissolution of the compositions of Examples 7-12.

The dissolution results (% active released over time) for these compression coated 20 mg and 120 mg tablets are presented in FIG. 3 and Tables 9 and 10 below.

TABLE 9

| Disso Time (h) | 20 mg Slow (G) % active released | 20 mg Med. (H) % active released | 20 mg Fast (I) % active released |
|---|---|---|---|
| 1 | 5 | 6 | 8 |
| 2 | 8 | 10 | 14 |
| 4 | 14 | 19 | 28 |
| 8 | 33 | 43 | 55 |
| 12 | 56 | 66 | 81 |
| 18 | 81 | 91 | 106 |
| 24 | 99 | 102 | 107 |

TABLE 10

| Disso Time (h) | 120 mg Slow (J) % active released | 120 mg Med. (K) % active released | 120 mg Fast (L) % active released |
|---|---|---|---|
| 1 | 5 | 6 | 8 |
| 2 | 8 | 10 | 15 |
| 4 | 14 | 20 | 29 |
| 8 | 35 | 47 | 57 |
| 12 | 59 | 72 | 82 |
| 18 | 86 | 100 | 98 |
| 24 | 102 | 103 | 100 |

As indicated by the dissolution of the above examples, factors which influence the dissolution of active agent from the dosage forms are the core:shell weight ratio and the tablet weight. Further, dissolution data presented above demonstrates that formulations of the present invention exhibit substantially zero order release as disclosed herein.

Example 13

A randomized, open-label, crossover study in healthy adult male and female subjects was conducted with the hydrocodone formulations (HYD) of Examples 7-12. The study was comprised of Iterations (a process of repeating the study design each time with a unique group of subjects undergoing a set of predefined treatments). The following Iterations were conducted:

Iteration 1:
N=36
Randomized, single-dose, 3 treatment, 3 period crossover.
  HYD 20 mg, slow release tablet, fasted state (Tablet G)
  HYD 20 mg, medium release tablet, fasted state (Tablet H)
  HYD 20 mg, fast release tablet, fasted state (Tablet I)
Iteration 2:
N=36
Randomized, single-dose, 3 treatment, 3 period crossover.
  HYD 120 mg, slow release tablet, fasted state (Tablet J)
  HYD 120 mg, medium release tablet, fasted state (Tablet K)
  HYD 120 mg, fast release tablet, fasted state (Tablet L)
Iteration 3:
N=16
Randomized, single-dose, 2 treatment, 2 period crossover.
  HYD 120 mg, slow release tablet, fasted state (Tablet J)
  HYD 120 mg, slow release tablet, fed state (Tablet J)
  The formulations were each administered orally with 8 oz. (240 mL) water as a single dose in the fasted or fed state as indicated.

As this study was conducted in healthy human subjects, the opioid antagonist naltrexone hydrochloride was administered to minimize opioid-related adverse events.

Subject Selection

Screening Procedures
The following screening procedures were performed for all potential subjects at a screening visit conducted within 28 days prior to first dose administration:
  Informed consent.
  Informed consent for optional pharmacogenomic sampling.
  Informed consent for optional hair sampling.
  Weight, height, body mass index (BMI), and demographic data.
  Evaluation of inclusion/exclusion criteria.
  Medical and medication history, including concomitant medication.
  Vital signs (systolic/diastolic blood pressure, pulse rate, respiration rate, oral temperature) after being seated for approximately 5 minutes and $SpO_2$
  Additional vital signs (systolic/diastolic blood pressure, and pulse rate) after standing for approximately 2 minutes.
  HDYF? Inquiry was performed at the same time vital signs were measured.
  Routine physical examination.
  Clinical laboratory evaluations following at least a 4 hour fast (including biochemistry, hematology, and urinalysis).
  12-lead ECG. QTcF not to exceed 450 msec.
  Screens for hepatitis (including hepatitis B surface antigen [HBsAg], hepatitis C antibody [anti-HCV]).
  Screens for alcohol, cotinine, and selected drugs of abuse.
  Serum pregnancy test, female subjects only; Serum follicle stimulating hormone (FSH) postmenopausal females only;
  Serum pregnancy test (female subjects only).
  Serum follicle stimulating hormone (FSH) test (postmenopausal females only).

Inclusion Criteria
  Subjects who met the following criteria were included in the study.
  Provided written informed consent.
  Males and females aged 18 to 50, inclusive.
  Body weight ranging from 50 to 100 kg (110 to 220 lbs) and a BMI 18 to 34 (kg/m$^2$), inclusive.
  Healthy and free of significant abnormal findings as determined by medical history, physical examination, vital signs, and ECG.
  Females of child-bearing potential must be using an adequate and reliable method of contraception (i.e, barrier with additional spermicidal foam or jelly, intrauterine device, hormonal contraception). Females who are post-menopausal must have been postmenopausal ≥1 year and have elevated serum FSH.
  Willing to eat the food supplied during the study.
  Will refrain from strenuous exercise during the entire study. Subjects will not begin a new exercise program nor participate in any unusually strenuous physical exertion.

Exclusion Criteria
The following criteria excluded potential subjects from the study.
  Females who are pregnant (positive beta human chorionic gonadotropin test) or lactating.
  Current or recent (within 5 years) history of drug or alcohol abuse.
  History or any current conditions that might interfere with drug absorption, distribution, metabolism or excretion.
  Use of an opioid-containing medication in the past 30 days preceding the initial dose in this study.
  History of known sensitivity to hydrocodone, naltrexone or related compounds.
  Any history of frequent nausea or emesis regardless of etiology.
  Any history of seizures or head trauma with sequelae.
  Participation in a clinical drug study during the 30 days preceding the initial dose in this study.
  Any significant illness during the 30 days preceding the initial dose in this study.
  Use of any medication including thyroid hormonal therapy (hormonal contraception is allowed), vitamins, herbal and/or mineral supplements during the 7 days preceding the initial dose.
  Abnormal cardiac conditions including any of the following:
    QTc interval ≥450 msec (calculated using Fridericia's correction) at screening.
    QTc interval ≥480 msec (calculated using Fridericia's correction) during Treatment period.
  Refusal to abstain from food 10 hours preceding and 4 hours following study drug administration and to abstain from caffeine or xanthine containing beverages entirely during each confinement.
  Refusal to abstain from consumption of alcoholic beverages 48 hours prior to initial study drug administration (day 1) and anytime during study.
  History of smoking or use of nicotine products within 45 days of study drug administration or a positive urine cotinine test.
  Blood or blood products donated within 60 days prior to study drug administration or anytime during the study and for 30 days after completion of the study, except as required by this protocol.

Plasma donated within 14 days prior to study drug administration or any time during the study, except as required by this protocol.

Positive results of urine drug screen or alcohol screen.

Positive results of HBsAg, anti-HCV.

Positive naloxone HCl challenge test.

Presence of Gilbert's Syndrome, or any known hepatobiliary abnormalities.

For the optional hair sampling portion of the study only, an insufficient amount of scalp hair to provide an adequate sample.

The investigator believes the subject to be unsuitable for reason(s) not specifically stated in the exclusion criteria.

Subjects meeting all the inclusion criteria and none of the exclusion criteria were randomized into the study.

Each subject was assigned a unique subject number at screening. Assignment of subject numbers was in ascending order and no numbers were omitted. Subject numbers were used on all study documentation.

Check-In Procedures

On Day −1 of Period 1 only, subjects were admitted to the study unit and received a Naloxone HCl challenge test. The results of the test had to be negative for subjects to continue in the study. Vital signs and $SPO_2$ were measured prior to and following the Naloxone HCl.

The following procedures were also performed for all subjects at Check-in for each period:

Verification of inclusion/exclusion criteria, including verification of willingness to comply with caffeine and xanthine restriction criteria.

Vital signs (after being seated for approximately 5 minutes) and $SpO_2$.

HDYF (How do you feel)? Inquiry was performed at the same time vital signs were measured.

Clinical laboratory evaluations (day −1, period 1 only) including biochemistry (fasting for at least 4 hours), hematology, and urinalysis) were collected after vital signs and $SpO_2$ were measured.

Screen for alcohol (via urine or blood alcohol or breathalyzer test), cotinine, and selected drugs of abuse (via urine testing).

Urine pregnancy test (for all female subjects).

Concomitant medication monitoring and recording.

AE monitoring and recording.

For subjects to continue their participation in the study, the results of the drug screen (including alcohol and cotinine) had to be available and negative prior to dosing. In addition, continued compliance with concomitant medication and other restrictions were verified at Check-in and throughout the study in the appropriate source documentation.

Treatment Period Procedures

Treatments to be studied were predetermined for each Iteration. Within an Iteration, as data became available, treatments were dropped between cohorts. Dropped treatments were replaced with repeats of remaining treatments.

Prior to the first dose in period 1, subjects were randomized to a treatment sequence.

Subjects received naltrexone HCl tablets (50 mg) with 240 mL of water at −12 h prior to study drug dosing.

Prior to study drug administration (except period 1), subjects had chemistry (fasting for at least 4 hours), hematology and urinalysis tests performed.

Subjects were administered the study drug with 240 mL of water as follows:

For Fasted Treatment:
Following a 10-hour overnight fast, subjects were administered study drug with 240 mL of water. Subjects receiving fasted treatment continued fasting from food for 4 hours following dosing.

For Fed Treatments:
Following a 10-hour overnight fast, the subjects were fed a standard meal (FDA high-fat breakfast) 30 minutes prior to administration of study drug with 240 mL of water. No food was allowed for at least 4 hours post-dose. It was made very clear to the subjects that all of the meal should be consumed within the designated time-frame.

Subjects were standing or in an upright sitting position while receiving their dose of study drug.

Fasting was not required for nondosing study days.

Subjects received naltrexone HCl 50-mg tablets with 240 mL of water at −12, 0, 12, 24, and 36 hours relative to each study drug dosing.

For subjects receiving hydrocodone doses of 60 mg or more, $SpO_2$ was monitored continuously beginning prior to dosing and continuing through 24 hours post-dose.

Vital signs (after being seated for approximately 5 minutes) and $SpO_2$, were obtained pre-dose and at hour 1, 2, 4, 6, 8, 12, 24, 36, 48, and 72 hour post dose for each period.

HDYF (How do you feel)? Inquiry was performed at the same time vital signs were measured.

Subjects had biochemistry (fasting for at least 4 hours), hematology, and urinalysis tests performed 24 hours post-dose.

In addition, 12-lead ECGs were performed for each subject pre-dose and approximately 12, 24 and 48 hours post-dose. If QTcF exceeded 480 msec the subject was discontinued due to the reason of Adverse Event.

Blood samples for determining hydrocodone plasma concentrations were obtained for each subject at pre-dose and at 0.5, 1, 1.5, 2, 2.5, 3, 3.5, 4, 5, 6, 8, 10, 12, 14, 18 24, 36, 48, and 72 hours post-dose for each period.

Subjects were confined to the unit from check-in to the unit on the day before dosing until the time that their 48 h procedures were completed. The subjects returned to the unit for the 72 h procedures.

During the study, AEs and concomitant medications were recorded.

In addition, the subjects were informed that it is very important to report any/all episodes of emesis to the study staff immediately and that this information is crucial to the proper conduct and outcome of the trial. The subjects were informed that they would not be penalized in any way due to reporting cases of emesis. The study staff was instructed to carefully document any/all cases of emesis.

Study Completion Procedures

The following procedures were performed at the study site for all subjects at end-of-study (study completion), 7 to 10 days after receiving their last dose of study drug or upon early discontinuation from the study.

Concomitant medication evaluation.

Vital signs (after being seated for approximately 5 minutes) and $SpO_2$.

HDYF? Inquiry was performed at the same time vital signs are measured.

Physical examination.

12-Lead ECG.

Clinical laboratory evaluations (including biochemistry [fasted at least 4 hours], hematology, and urinalysis).

AE evaluations.

Serum pregnancy test (for female subjects only).

Figure 4:
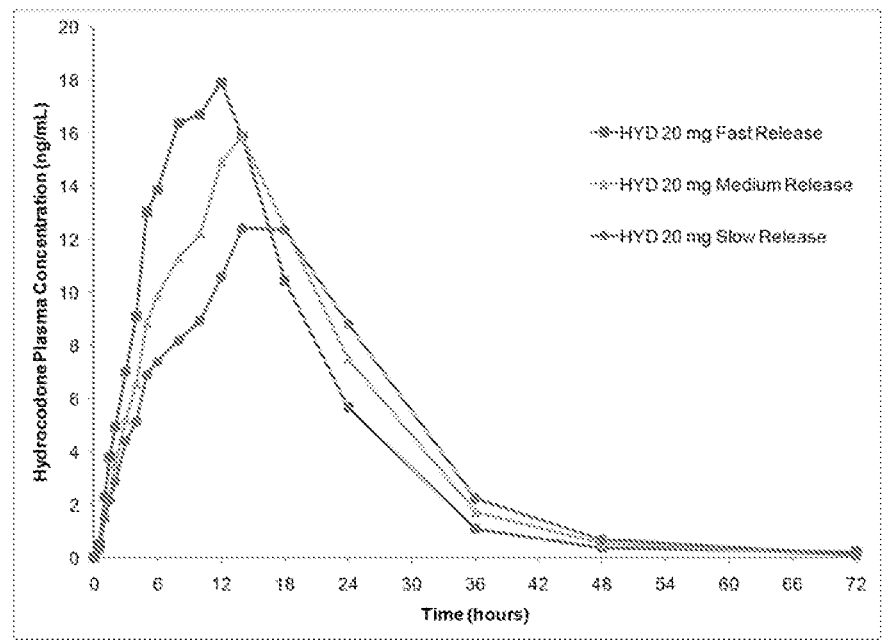
FIG. 4 is a graph that depicts the mean plasma concentration time curve of Iteration 1 of Example 13.
Figure 5:
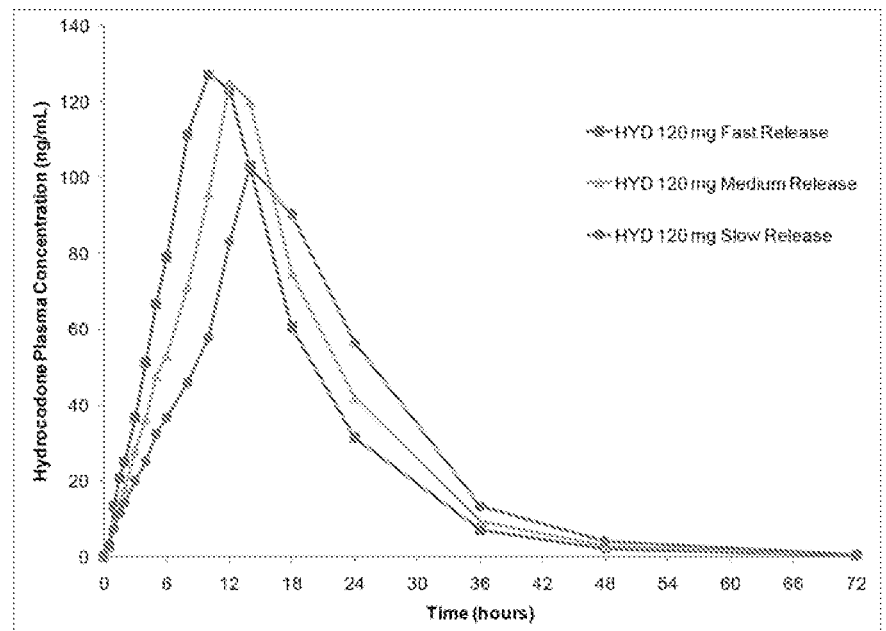
FIG. 5 is a graph that depicts the mean plasma concentration time curve of Iteration 2 of Example 13.
Figure 6:
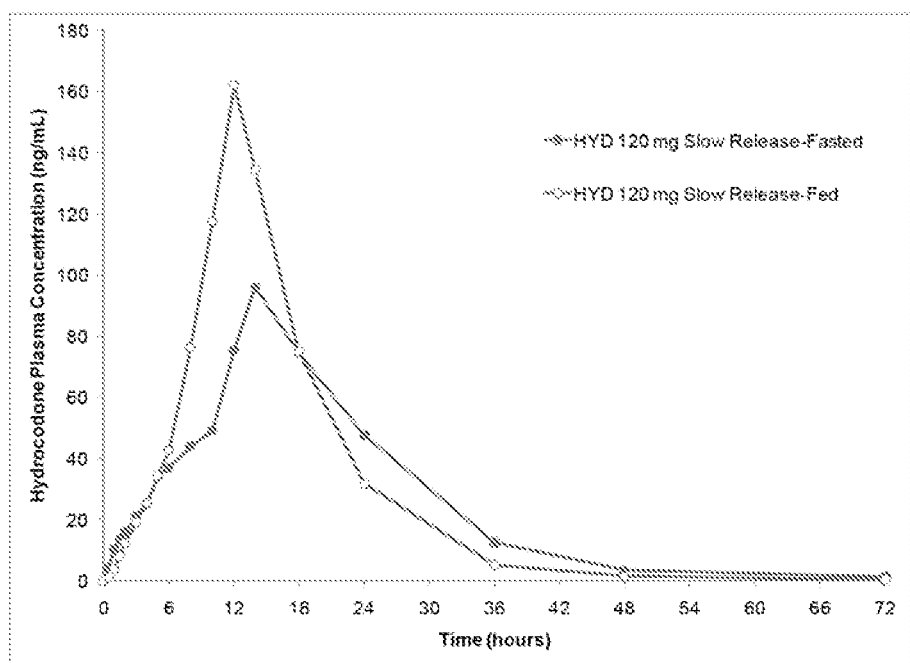
FIG. 6 is a graph that depicts the mean plasma concentration time curve of Iteration 3 of Example 13.

The draft results are set forth in FIGS. 4-6 and Table 13 below:

TABLE 13

Summary of Draft Plasma Hydrocodone Pharmacokinetic Parameters

| Parameter (Unit) | Statistic | Iteration 1: HYD 20 mg | | | Iteration 2: HYD 120 mg | | | Iteration 3: HYD 120 mg | |
|---|---|---|---|---|---|---|---|---|---|
| | | Slow (G) Fasted (N = 36) | Medium (H) Fasted (N = 36) | Fast (I) Fasted (N = 36) | Slow (J) Fasted (N = 36) | Medium (K) Fasted (N = 36) | Fast (L) Fasted (N = 36) | Slow (J) Fasted (N = 14) | Slow (J) Fed (N = 16) |
| AUCt (ng*h/mL) | MEAN | 302 | 323 | 330 | 2028 | 2074 | 2048 | 1921 | 2025 |
| | SD | 138 | 101 | 90 | 439 | 440 | 514 | 369 | 420 |
| | MIN | 43 | 95 | 78 | 1315 | 1043 | 430 | 1417 | 1135 |
| | MAX | 619 | 557 | 499 | 2911 | 2869 | 2917 | 2586 | 2716 |
| AUCinf (ng*h/mL) | Mean | 312 | 326 | 329 | 2037 | 2083 | 2055 | 1933 | 2032 |
| | SD | 142 | 102 | 90 | 442 | 443 | 516 | 374 | 420 |
| | Min | 44 | 97 | 83 | 1320 | 1046 | 430 | 1427 | 1136 |
| | Max | 623 | 564 | 507 | 2935 | 2908 | 2924 | 2594 | 2717 |
| Cmax (ng/ml) | Mean | 15.0 | 17.4 | 20.9 | 119 | 138 | 142 | 110 | 166 |
| | SD | 6.4 | 5.8 | 7.2 | 35.8 | 35.3 | 39.3 | 30 | 34.2 |
| | Min | 4.3 | 7.5 | 7.7 | 55.2 | 76.7 | 35.6 | 67 | 96.2 |
| | Max | 30.7 | 31.3 | 39.0 | 227 | 241 | 239 | 162 | 240 |
| Tmax (h) | Mean | 15.2 | 13.7 | 11.4 | 15.4 | 12.7 | 10.7 | 15 | 12.0 |
| | SD | 4.7 | 2.6 | 3.5 | 2.9 | 1.7 | 2.0 | 3 | 1.0 |
| | Min | 5 | 8 | 6 | 10 | 10 | 6 | 12 | 10 |
| | Median | 14 | 14 | 12 | 14 | 12 | 10 | 14 | 12 |
| | Max | 24 | 18 | 24 | 24 | 18 | 14 | 24 | 14 |
| T1/2 (h) | Mean | 8.3 | 7.6 | 9.0 | 7.1 | 7.6 | 7.1 | 7.7 | 7.8 |
| | SD | 3.1 | 2.9 | 4.9 | 2.4 | 3.3 | 2.5 | 2.4 | 4.6 |
| | Min | 4.1 | 4.5 | 4.4 | 4.5 | 4.2 | 4.1 | 4.0 | 3.8 |
| | Max | 15.3 | 17.3 | 25.2 | 16.0 | 17.9 | 13.4 | 12.4 | 21.4 |
| Tlag (h) | Mean | 0.15 | 0.11 | 0.13 | 0.06 | 0.03 | 0.01 | 0.03 | 0.06 |
| | SD | 0.23 | 0.21 | 0.22 | 0.16 | 0.12 | 0.09 | 0.13 | 0.17 |
| | Min | 0 | 0 | 0 | 0 | 0 | 0 | 0 | 0 |
| | Max | 0.5 | 0.5 | 0.5 | 0.5 | 0.5 | 0.5 | 0.5 | 0.5 |
| C24/Cmax | Mean | 0.57 | 0.45 | 0.30 | 0.52 | 0.32 | 0.23 | N/A | N/A |
| | SD | 0.28 | 0.20 | 0.18 | 0.21 | 0.15 | 0.10 | N/A | N/A |
| | Min | 0.03 | 0.10 | 0.06 | 0.17 | 0.11 | 0.07 | N/A | N/A |
| | Max | 1.00 | 0.84 | 1.00 | 1.00 | 0.74 | 0.48 | N/A | N/A |

Examples 14-20

Seven different compression coated tablets (designated as Tablets M-S) containing a total of 20, 30, 40, 60, 80, 100 or 120 mg of hydrocodone bitartrate, respectively, were prepared according to Tables 14 (Tablets M, N, O, P) and 15 (Tablets Q, R, S) below.

TABLE 14

(Tablets M, N, O, P)

| Component | Formulation M (20 mg) mg/tablet | Formulation N (30 mg) mg/tablet | Formulation O (40 mg) mg/tablet | Formulation P (60 mg) mg/tablet |
|---|---|---|---|---|
| Core | | | | |
| Hydrocodone Bitartrate | 16.000 | 24.000 | 32.000 | 48.000 |
| Microcrystalline Cellulose, Avicel PH 101 | 1.091 | 1.636 | 2.182 | 3.273 |
| Hydroxypropyl Cellulose, Klucel EXF | 1.091 | 1.636 | 2.182 | 3.273 |
| Purified Water | | | | |
| PEO (Mw = 600,000) POLYOX WSR 205 FP | 279.918 | 270.827 | 261.736 | 243.555 |
| Magnesium Stearate | 1.500 | 1.500 | 1.500 | 1.500 |
| FD&C Yellow No. 6 Aluminum Lake | 0.400 | 0.400 | 0.400 | 0.400 |
| Subtotal | 300 | 300 | 300 | 300 |
| Dry Coat | | | | |
| Hydrocodone Bitartate | 4.000 | 6.000 | 8.000 | 12.000 |
| Microcrystalline Cellulose, Avicel PH 101 | 0.273 | 0.409 | 0.545 | 0.818 |
| Hydroxypropyl Cellulose, Klucel EXF | 0.273 | 0.409 | 0.545 | 0.818 |
| Purified Water | | | | |
| PEO (Mw = 7,000,000) POLYOX WSR 303 FP | 393.455 | 391.182 | 388.909 | 384.364 |
| Magnesium Stearate | 2.000 | 2.000 | 2.000 | 2.000 |
| Subtotal | 400 | 400 | 400 | 400 |
| Cosmetic Coat | | | | |
| Opadry Clear 85F19250 | 14 | 14 | 14 | 14 |
| Opadry Green 85F110049 | 21 | | | |
| Opadry Yellow 85F120034 | | 21 | | |
| Opadry Gray 85F175009 | | | 21 | |

TABLE 14-continued (Tablets M, N, O, P)

| Component | Formulation M (20 mg) mg/tablet | Formulation N (30 mg) mg/tablet | Formulation O (40 mg) mg/tablet | Formulation P (60 mg) mg/tablet |
|---|---|---|---|---|
| Opadry Beige 85F170015 | | | | 21 |
| Opadry Pink 85F140044 | | | | |
| Opadry Blue 85F105039 | | | | |
| Opadry White 85F18422 | | | | |
| Total | 735 | 735 | 735 | 735 |

TABLE 15

(Tablets Q, R, S)

| Component | Formulation Q (80 mg) mg/tablet | Formulation R (100 mg) mg/tablet | Formulation S (120 mg) mg/tablet |
|---|---|---|---|
| Core | | | |
| Hydrocodone Bitartrate | 64.000 | 80.000 | 96.000 |
| Microcrystalline Cellulose, Avicel PH 101 | 4.364 | 5.455 | 6.545 |
| Hydroxypropyl Cellulose, Klucel EXF | 4.364 | 5.455 | 6.545 |
| Purified Water | | | |
| PEO (Mw = 600,000) POLYOX WSR 205 FP | 225.373 | 207.191 | 189.009 |
| Magnesium Stearate | 1.500 | 1.500 | 1.500 |
| FD&C Yellow No. 6 Aluminum Lake | 0.400 | 0.400 | 0.400 |
| Subtotal | 300 | 300 | 300 |
| Dry Coat | | | |
| Hydrocodone Bitartrate | 16.000 | 20.000 | 24.000 |
| Microcrystalline Cellulose, Avicel PH 101 | 1.091 | 1.364 | 1.636 |
| Hydroxypropyl Cellulose, Klucel EXF | 1.091 | 1.364 | 1.636 |
| Purified Water | | | |
| PEO (Mw = 7,000,000) POLYOX WSR 303 FP | 379.818 | 375.273 | 370.727 |
| Magnesium Stearate | 2.000 | 2.000 | 2.000 |
| Subtotal | 400 | 400 | 400 |
| Cosmetic Coat | | | |
| Opadry Clear 85F19250 | 14 | 14 | 14 |
| Opadry Green 85F110049 | | | |
| Opadry Yellow 85F120034 | | | |
| Opadry Gray 85F175009 | | | |
| Opadry Beige 85F170015 | | | |
| Opadry Pink 85F140044 | 21 | | |
| Opadry Blue 85F105039 | | 21 | |
| Opadry White 85F18422 | | | 21 |
| Total | 735 | 735 | 735 |

A high shear mixer was charged with the hydrocodone bitartrate, the microcrystalline cellulose, and the hydroxypropyl cellulose.

The dry mix mixture was mixed for one (1) minute at low speed and the chopper off, then mixed at high speed with the chopper on. Water was added to the mixture until the desired amount of water had been added, producing a wet granulation.

The wet granulation was then passed through a screening mill to de-lump, and transferred to a fluid bed dryer to dry. The dry mixture was then passed through a fine mesh screen until the target particle size range was achieved (<1.0%).

The dried screened granulation was then passed through a screening mill and the active granulation was collected in stainless steel containers. A V-blender was charged with approximately half of the polyethylene oxide (POLYOX WSR-205); the appropriate amount of active granulation (adjusted for assay); the aluminum lake; and the remaining polyethylene oxide (POLYOX WSR-205), and the mixture was blended for 10 minutes.

The V-blender was then charged with the magnesium stearate and the mixture was blended for 2 minutes and discharged into stainless steel drums.

A V-blender was charged with approximately half of the polyethylene oxide (POLYOX WSR-303); the appropriate amount of active granulation (adjusted for assay); and the remaining polyethylene oxide (POLYOX WSR-303), and the mixture was blended for 10 minutes.

The V-blender was then charged with the magnesium stearate; blended for 2 minutes and discharged into stainless steel drums.

The left side of the press was set up with 8.75 mm, round, shallow concave tooling, and the right side of the press with 12 mm, round, shallow concave, bevel edge tooling.

The core blend (colored) was then charged into the left side hopper (gravity feed system) to initiate core compression.

The core weight was adjusted to the target weight (300 mg, +/−5%).

The dry coat blend (white to off white) was then charged into the right side hopper (gravity feed system) to initiate tablet compression.

The initial dry coat fill and subsequent dry coat fill were adjusted after core placement to the target total tablet weight of 700 mg (300 mg core+400 mg dry coat).

For the Opadry color dispersion (target 20% solids), a mixing vessel was charged with the appropriate amount of purified water the mixer speed was adjusted to form a vortex. Opadry color powder was added to the vessel over a period of 2-5 minutes, and mixed until a homogenous dispersion is produced (minimum 1 hour).

For the Opadry clear dispersion (target 7.5% solids) a separate mixing vessel was charged with the appropriate amount of purified water and the mixer speed was adjusted to form a vortex. Opadry clear powder was added to the vessel over a period of 2-5 minutes (target 3 min), and mixed until a homogenous dispersion is produced (minimum 1 hour).

The compression coated tablets were then transferred to a perforated coating pan and film-coated with the Opadry color dispersion to a target weight gain of 0.7%-1.5%.

The heating temperature was increased and the tablets were cured to a target exhaust temperature of 72° C. for approximately 30 minutes, then cooled.

The tablet coating was continued with the Opadry color dispersion to a target weight gain of 3% including the weight gain from the previous coating.

The tablets were then film-coated with the Opadry clear dispersion to a final target weight gain of 5%.

The dissolution results (% active released over time) for these compression coated 20 mg, 30 mg, 40 mg, 60 mg, 80 mg, 100 mg, and 120 mg tablets are presented in Table 16 below.

TABLE 16

The Dissolution Results of Compression Coated 20, 40, 60, 80, 120 mg Tablets (SGF, n = 12)

| Diss Time (h) | 20 mg % active released | 40 mg % active released | 60 mg % active released | 80 mg % active released | 120 mg % active released |
|---|---|---|---|---|---|
| 1  | 4  | 4   | 4   | 5   | 4   |
| 2  | 7  | 7   | 7   | 7   | 7   |
| 4  | 13 | 13  | 13  | 13  | 14  |
| 6  | 21 | 21  | 21  | 21  | 22  |
| 8  | 31 | 32  | 32  | 31  | 32  |
| 10 | 42 | 43  | 44  | 43  | 45  |
| 12 | 53 | 55  | 55  | 55  | 57  |
| 14 | 62 | 65  | 66  | 65  | 68  |
| 16 | 71 | 74  | 75  | 74  | 77  |
| 18 | 79 | 82  | 83  | 83  | 86  |
| 20 | 87 | 91  | 92  | 91  | 93  |
| 22 | 95 | 99  | 98  | 98  | 99  |
| 24 | 99 | 102 | 102 | 101 | 101 |

Example 21

A randomized, open-label, single-dose, 5-treatment, 4-period crossover, incomplete block study in healthy adult male and female subjects was conducted with the hydrocodone formulations (HYD) of Examples 14-20. The study was comprised of a maximum of 5 treatments, across 4 periods.

The HYD tablet strength, or doses studied were:
1×20 mg HYD tablet
1×40 mg HYD tablet
1×60 mg HYD tablet
1×80 mg HYD tablet
1×120 mg HYD tablet The treatments were each administered orally with 8 oz. (240 mL) water as a single dose in the fasted state.

As this study was conducted in healthy human subjects, the opioid antagonist naltrexone hydrochloride was administered to minimize opioid-related adverse events.

Subject Selection

Screening Procedures
The following screening procedures were performed for all potential subjects at a screening visit conducted within 28 days prior to first dose administration:
  Informed consent.
  Informed consent for optional pharmacogenomic sampling.
  Informed consent for optional hair sampling.
  Weight, height, body mass index (BMI), and demographic data.
  Evaluation of inclusion/exclusion criteria.
  Medical and medication history, including concomitant medication.
  Vital signs (systolic/diastolic blood pressure, pulse rate, respiration rate, oral temperature) after being seated for approximately 5 minutes and SpO$_2$
  Additional vital signs (systolic/diastolic blood pressure, and pulse rate) after standing for approximately 2 minutes.
  HDYF? Inquiry was performed at the same time vital signs were measured.
  Routine physical examination.
  Clinical laboratory evaluations following at least a 4 hour fast (including biochemistry, hematology, and urinalysis).
  12-lead ECG. QTcF not to exceed 450 msec.
  Screens for hepatitis (including hepatitis B surface antigen [HBsAg], hepatitis C antibody [anti-HCV]).
  Screens for alcohol, cotinine, and selected drugs of abuse.
  Serum pregnancy test, female subjects only; Serum follicle stimulating hormone (FSH) postmenopausal females only;
  Serum pregnancy test (female subjects only).
  Serum follicle stimulating hormone (FSH) test (postmenopausal females only).

Inclusion Criteria
Subjects who met the following criteria were included in the study.
  Provide written informed consent.
  Males and Females aged 18 to 50, inclusive.
  Willing to eat the food supplied during the study.
  Body weight ranging from 50 to 100 kg (110 to 220 lbs) and a BMI of 18 to 30 (kg/m$^2$), inclusive.
  Willing to refrain from strenuous exercise through the end of study visit. Subjects will not begin a new exercise program nor participate in any unusually strenuous physical exertion.
  Healthy and free of significant abnormal findings as determined by medical history, physical examination, clinical laboratory values, vital signs, and ECG.
  Females of child-bearing potential must be using an adequate and reliable method of contraception (ie, barrier with additional spermicidal foam or jelly, intrauterine device, hormonal contraception). Females who are postmenopausal must have been postmenopausal ≥1 year and have elevated serum FSH.

Exclusion Criteria
The following criteria excluded potential subjects from the study.
  Females who are pregnant (positive beta human chorionic gonadotropin test) or lactating.
  Current or recent (within 5 years) history of drug or alcohol abuse.
  History or any current conditions that might interfere with drug absorption, distribution, metabolism or excretion.
  Use of an opioid-containing medication in the past 30 days preceding the initial dose of study drug in this study.
  History of known sensitivity to hydrocodone, naltrexone, or related compounds.
  Any history of frequent nausea or emesis regardless of etiology.
  Any history of seizures or head trauma with sequelae.
  Participation in a clinical drug study during the 30 days preceding the initial dose of study drug in this study.
  Any significant illness during the 30 days preceding the initial dose of study drug in this study.
  Use of any medication including thyroid hormonal therapy (hormonal contraception and hormonal replacement therapy in the form of estrogen with or without progestin is allowed), vitamins, herbal and/or mineral supplements during the 7 days preceding the initial dose of study drug.
  Any personal or family history of prolonged QT interval or disorders of cardiac rhythm.
  Abnormal cardiac conditions including any of the following:
    QTc interval ≥450 msec (calculated using Fridericia's correction) at screening
    QTc interval ≥480 msec (calculated using Fridericia's correction) during the treatment period.

Refusal to abstain from food 10 hours preceding and 4 hours following study drug administration and to abstain from caffeine or xanthine containing beverages entirely during each confinement.

Refusal to abstain from consumption of alcoholic beverages 48 hours prior to initial study drug administration (day 1) and any time through the end of study visit.

Blood or blood products donated within 30 days prior to initial study drug administration or anytime through the end of study visit, except as required by this protocol.

History of smoking or use of nicotine products within 45 days of initial study drug administration or a positive urine cotinine test.

Positive results of urine drug screen or alcohol screen.

Positive results of HBsAg, anti-HCV.

Positive naloxone HCl challenge test.

Presence of Gilbert's Syndrome, or any known hepatobiliary abnormalities.

The investigator believes the subject to be unsuitable for reason(s) not specifically stated in the exclusion criteria.

Subjects meeting all the inclusion criteria and none of the exclusion criteria were randomized into the study.

Each subject was assigned a unique subject number at screening. Assignment of subject numbers was in ascending order and no numbers were omitted. Subject numbers were used on all study documentation.

Check-In Procedures

On Day −1 of Period 1 only, subjects were admitted to the study unit and received a Naloxone HCl challenge test. The results of the test had to be negative for subjects to continue in the study. Vital signs and $SPO_2$ were measured prior to and following the Naloxone HCl.

The following procedures were also performed for all subjects at Check-in for each period:

Verification of inclusion/exclusion criteria, including verification of willingness to comply with caffeine and xanthine restriction criteria.

Vital signs (after being seated for approximately 5 minutes) and $SpO_2$.

HDYF (How do you feel)? Inquiry was performed at the same time vital signs were measured.

Clinical laboratory evaluations (day −1, period 1 only) including biochemistry (fasting for at least 4 hours), hematology and urinalysis) were collected after vital signs and $SpO_2$ were measured.

Screen for alcohol (via urine or blood alcohol or breathalyzer test), cotinine, and selected drugs of abuse (via urine testing).

Urine pregnancy test (for all female subjects).

Concomitant medication monitoring and recording.

AE monitoring and recording.

For subjects to continue their participation in the study, the results of the drug screen (including alcohol and cotinine) had to be available and negative prior to dosing. In addition, continued compliance with concomitant medication and other restrictions were verified at Check-in and throughout the study in the appropriate source documentation.

Treatment Period Procedures

Treatments to be studied were predetermined for each Iteration. Within an Iteration, as data became available, treatments were dropped between cohorts. Dropped treatments were replaced with repeats of remaining treatments.

Prior to the first dose in period 1, subjects were randomized to a treatment sequence.

Subjects received naltrexone HCl tablets (50 mg) with 240 mL of water at −12 h prior to study drug dosing.

Subjects were administered the study drug with 240 mL of water as following a 10-hour overnight fast. Subjects continued fasting from food for 4 hours following dosing.

Subjects were standing or in an upright sitting position while receiving their dose of study drug.

Fasting was not required for nondosing study days.

Subjects received naltrexone HCl 50-mg tablets with 240 mL of water at −12, 0, 12, 24, and 36 hours relative to each study drug dosing.

For subjects receiving hydrocodone doses of 60 mg or more, $SpO_2$ was monitored continuously beginning prior to dosing and continuing through 24 hours post-dose.

Vital signs (after being seated for approximately 5 minutes) and $SpO_2$, were obtained pre-dose and at hour 1, 2.5, 4, 6, 8, 12, 24, 36, 48, and 72 hour post dose for each period.

HDYF (How do you feel)? Inquiry was performed at the same time vital signs were measured.

12-lead ECGs were performed for each subject pre-dose and approximately 12, 24 and 48 hours post-dose.

Blood samples for determining hydrocodone plasma concentrations were obtained for each subject at pre-dose and at 0.5, 1, 2.5, 4, 6, 8, 10, 12, 14, 16, 18, 24, 36, 48, and 72 hours post-dose for each period.

Subjects were confined to the unit from check-in to the unit on the day before dosing until the time that their 72 h procedures were completed.

During the study, AEs and concomitant medications were recorded.

In addition, the subjects were informed that it is very important to report any/all episodes of emesis to the study staff immediately and that this information is crucial to the proper conduct and outcome of the trial. The subjects were informed that they would not be penalized in any way due to reporting cases of emesis. The study staff was instructed to carefully document any/all cases of emesis.

Study Completion Procedures

The following procedures were performed at the study site for all subjects at end-of-study (study completion), 7 to 10 days after receiving their last dose of study drug or upon early discontinuation from the study.

Concomitant medication evaluation.

Vital signs (after being seated for approximately 5 minutes) and $SpO_2$.

HDYF? Inquiry was performed at the same time vital signs are measured.

Physical examination.

12-Lead ECG.

Clinical laboratory evaluations (including biochemistry [fasted at least 4 hours], hematology, and urinalysis).

AE evaluations.

Serum pregnancy test (for female subjects only).

Figure 7:
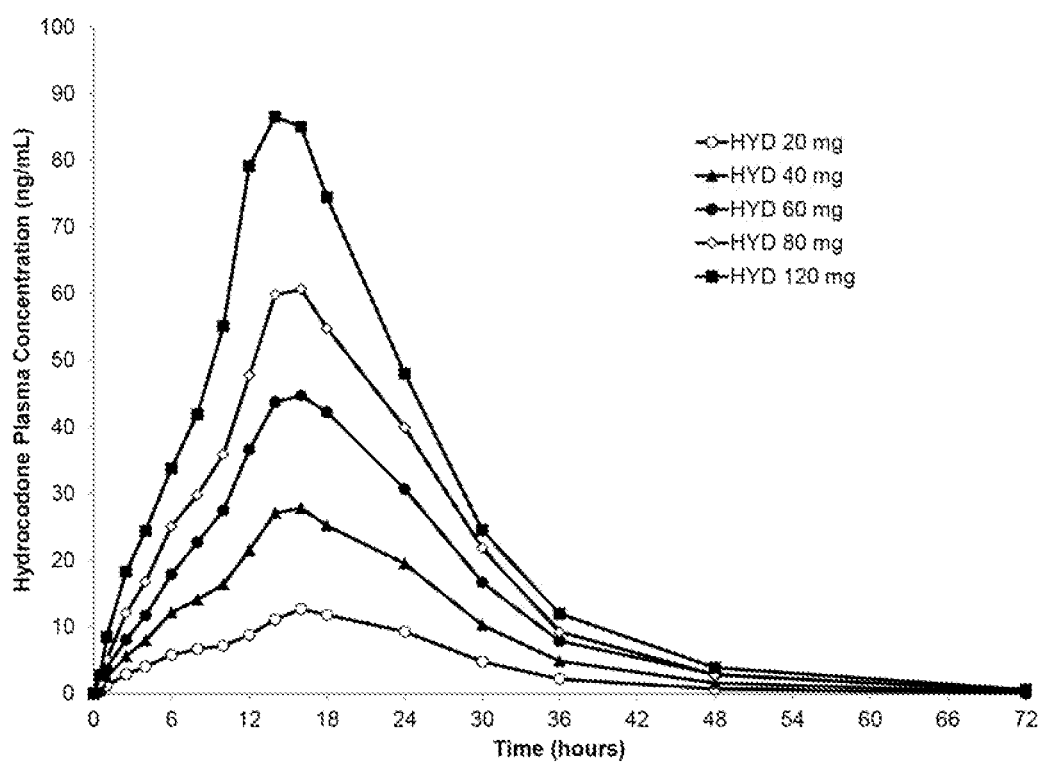
FIG. 7 is a graph that depicts the plasma concentrations of the compositions of Examples 14-20.

The draft results are set forth in FIG. 7 and Table 17 below:

TABLE 17

Summary of Draft Plasma Hydrocodone Pharmacokinetic Parameters

| Parameter (Unit) | Statistic | HYD 20 mg (N = 29) | HYD 40 mg (N = 30) | HYD 60 mg (N = 28) | HYD 80 mg (N = 30) | HYD 120 mg (N = 29) |
|---|---|---|---|---|---|---|
| AUCt (ng*h/mL) | MEAN | 281 | 618 | 1004 | 1298 | 1759 |
|  | SD | 127 | 255 | 292 | 373 | 671 |
|  | MIN | 30 | 85 | 580 | 559 | 303 |
|  | MAX | 591 | 1200 | 1724 | 2501 | 3324 |
| AUCinf (ng*h/mL) | Mean | 284 | 622 | 1009 | 1304 | 1768 |
|  | SD | 128 | 256 | 294 | 375 | 674 |
|  | Min | 31 | 86 | 583 | 564 | 305 |
|  | Max | 595 | 1213 | 1742 | 2514 | 3347 |
| Cmax (ng/ml) | Mean | 15 | 34 | 54 | 69 | 110 |
|  | SD | 5.5 | 12 | 15 | 17 | 44 |
|  | Min | 3.5 | 7.6 | 33 | 40 | 28 |
|  | Max | 26 | 54 | 83 | 109 | 199 |
| Tmax (h) | Mean | 15 | 16 | 16 | 15 | 15 |
|  | SD | 4.5 | 4.5 | 4.7 | 2.6 | 4.4 |
|  | Min | 6 | 6 | 10 | 10 | 6 |
|  | Median | 16 | 16 | 14 | 16 | 14 |
|  | Max | 24 | 24 | 30 | 24 | 30 |

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

What is claimed is:

1. A method of treating pain in a subject, comprising:
    administering to the subject a solid controlled release dosage form, the solid controlled release dosage form comprising:
        a core comprising a first portion of an opioid analgesic dispersed in a first matrix material, wherein the opioid analgesic comprises oxycodone, a pharmaceutically acceptable salt thereof or combinations thereof; and
        a shell encasing the core and comprising a second portion of the opioid analgesic dispersed in a second matrix material,
        wherein the dosage form further comprises acetaminophen;
        wherein the amount of opioid analgesic released from the dosage form is proportional within 20% to elapsed time from 8 to 24 hours, as measured by an in-vitro dissolution in a USP Apparatus 1 (basket) at 100 rpm in 900 ml simulated gastric fluid without enzymes (SGF) at 37° C.

2. The method of claim 1, wherein the core is a compressed tablet.

3. The method of claim 1, wherein the shell is a compression coating.

4. The method of claim 1, wherein the first matrix material comprises polyethylene oxide.

5. The method of claim 1, wherein the second matrix material comprises polyethylene oxide.

6. The method of claim 1, wherein both the first matrix material and the second matrix material comprise polyethylene oxide.

7. The method of claim 6, wherein the polyethylene oxide in the second matrix material has a higher viscosity than the polyethylene oxide in the first matrix material.

8. The method form of claim 1, wherein the first matrix material comprises polyethylene oxide having an average molecular weight from about 300,000 to about 10,000,000.

9. The method of claim 1, wherein the first matrix material comprises polyethylene oxide having an average molecular weight from about 500,000 to about 1,000,000.

10. The method of claim 1, wherein the second matrix material comprises polyethylene oxide having an average molecular weight from about 1,000,000 to about 10,000,000.

11. The method of claim 1, wherein the second matrix material comprises polyethylene oxide having an average molecular weight from about 6,000,000 to about 8,000,000.

12. The method of claim 6, wherein the polyethylene oxide in the second matrix material has an average molecular weight from about 4,000,000 to about and the polyethylene oxide in the first matrix material has an average molecular weight from about 300,000 to about 3,000,000.

13. The method of claim 6, wherein the polyethylene oxide in the second matrix material has an average molecular weight from about 6,000,000 to about 8,000,000 and the polyethylene oxide in the first matrix material has an average molecular weight from about 500,000 to about 1,000,000.

14. The method of claim 1, wherein the weight ratio of the core to the shell is from about 1:0.5 to about 1:5.

15. The method of claim 1, wherein the weight ratio of the core to the shell is from about 1:0.6 to about 1:1.5.

16. The method of claim 1, wherein the weight ratio of the core to the shell is from about 1:0.8 to about 1:1.2.

17. The method of claim 4, wherein the weight ratio of the first portion of opioid analgesic to polyethylene oxide in the first matrix material is from about 1:0.5 to about 1:100.

18. The method of claim 4, wherein the weight ratio of the first portion of opioid analgesic to polyethylene oxide in the first matrix material is from about 1:1 to about 1:10.

19. The method of claim 4, wherein the weight ratio of the first portion of opioid analgesic to polyethylene oxide in the first matrix material is from about 1:1.5 to about 1:4.

20. The method of claim 5, wherein the weight ratio of the second portion of opioid analgesic to polyethylene oxide in the second matrix material is from about 1:2 to about 1:200.

* * * * *